United States Patent
Westwood et al.

(10) Patent No.: US 8,563,557 B2
(45) Date of Patent: Oct. 22, 2013

(54) PYRIMIDINE DERIVATIVES AND THEIR PHARMACEUTICAL USE

(75) Inventors: Nicholas James Westwood, Dundee (GB); Sonia Lain, Stockholm (SE); Federico Medda, Fife (GB)

(73) Assignees: University Court of the University of Dundee, Dundee (GB); University Court of the University of St Andrews, St. Andrews (GB)

( * ) Notice: Subject to any disclaimer, the term of this patent is extended or adjusted under 35 U.S.C. 154(b) by 0 days.

(21) Appl. No.: 13/122,097

(22) PCT Filed: Oct. 2, 2009

(86) PCT No.: PCT/GB2009/000236
§ 371 (c)(1),
(2), (4) Date: Jun. 17, 2011

(87) PCT Pub. No.: WO2010/038043
PCT Pub. Date: Apr. 8, 2010

(65) Prior Publication Data
US 2011/0245282 A1 Oct. 6, 2011

(30) Foreign Application Priority Data
Oct. 2, 2008 (GB) .................................. 0818063.0

(51) Int. Cl.
*A01N 43/54* (2006.01)
*C07D 239/42* (2006.01)

(52) U.S. Cl.
USPC .......................................... 514/256; 544/298

(58) Field of Classification Search
USPC .......................................... 544/298; 514/256
See application file for complete search history.

(56) References Cited

U.S. PATENT DOCUMENTS

2005/0079995 A1* 4/2005 Bedaloy et al. .................. 514/2

OTHER PUBLICATIONS

Bersuker, I. B.; Dimoglo, A. S.; Gorbachov, M. Yu. Corporate Source: Inst. Chem., Kishinev, USSR Source: Bioorganicheskaya Khimiya (1987), 13(1), 38-44.*
Baker, Bernard Randall; Kelley, James L. Corporate Source: Dep. of Chem., Univ. of California, Santa Barbara, CA, Source: Journal of Medicinal Chemistry (1970), 13(3), 461-7.*
Wamhoff et al., Heterocycles by capture reactions of opened acyl-lactones. IV. A simple synthesis of 5H-[1]benzopyrano- and 12H-naphtho[1',2':5,6]pyrano[2,3-d]pyrimidines Chemische Berichte (1967), 100(4), 1324-3 Coden: CHBEAM; ISSN: 0009-2940; German.*
Vippagunta et al.*
Bedalov, "Identification of a small molecule inhibitor of Sir2p", PNAS, vol. 98, No. 26, pp. 15113-15118, (2001).
Heltweg et al., "Antitumor activity of a small-molecule inhibitor of human silent information regulator 2 enzymes", Cancer Res., vol. 66, No. 8, pp. 4368-4377 (2006).
International Search Report from related PCT Patent Application No. PCT/GB2009/002367 mailed Feb. 2, 2010, now published as International Publication No. WO 2010/038043 on Apr. 8, 2010.
Lain et al., "Discovery, in vivo activity, and mechanism of action of a small-molecule p53 activator", Cancer Cell, vol. 13, No. 5, pp. 454-463 (2008).
Medda et al., "Novel cambinol analogs as sirtuin inhibitors: synthesis, biological evaluation, and rationalization of activity", J. Med. Chem., vol. 52, No. 9, pp. 2673-2682 (2009).
Outeiro et al., "Sirtuin 2 inhibitors rescue alpha-synuclein-mediated toxicity in models of Parkinson's disease", Science, vol. 317, No. 5837, pp. 516-519 (2007).

* cited by examiner

*Primary Examiner* — Paul V. Ward
(74) *Attorney, Agent, or Firm* — Susan T. Evans; McDermott Will & Emery LLP

(57) ABSTRACT

The invention provides a compound according to formula (I): wherein: X is O or S; Y is O or S; each Ar and Ar' is independently a mono-, bi- or tricyclic aryl or heteroaryl group optionally substituted with one or more substituents selected from halo, alkyl, aryl, heteroaryl, hydroxyl, nitro, amino, alkoxy, alkylthio, cyano, thio, ester, acyl and amido; each $R^2$ is independently hydrogen, halo, alkyl, aryl, heteroaryl, hydroxyl, nitro, amino, alkoxy, alkylthio, cyano and thio; and $R^1$ is as defined herein, or a physiologically acceptable salt, solvate, ester, amide or other physiologically functional derivative thereof.

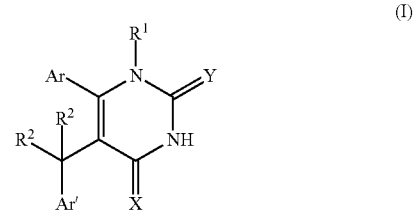

36 Claims, 2 Drawing Sheets

PYRIMIDINE DERIVATIVES AND THEIR PHARMACEUTICAL USE

This application is a U.S. National Stage of International Patent Application No. PCT/GB2009/002367, filed Oct. 2, 2009, which claims the benefit of priority to GB Application No. 0818063.0, filed Oct. 2, 2008, each of which is hereby incorporated by reference in its entirety.

INTRODUCTION

The present invention relates to compounds that have been found to activate the p53 tumour suppression protein. These compounds thus find use, for example, in the treatment of hyperproliferative diseases such as cancer.

BACKGROUND OF THE INVENTION

The central role that p53 plays in preventing tumour development is clear although ongoing research continues to dissect the details of how exactly this is achieved. Furthermore, a role for p53 in development, longevity and overall fitness of an organism is starting to emerge (Vousden K H, Lane D P, *Nat. Rev. Mol. Cell Biol.*, 2007 8(4):275-83). p53 acts as a transcriptional regulator, inducing the expression of a range of anti-proliferative target genes. More than 50% of adult human tumours are characterised by inactivating mutations or deletions of the P53 gene. Other tumour types in which p53 is wild-type frequently have alterations in the mechanisms that control p53 activation. It is accepted that activation of the p53 tumour suppressor protein through the use of non-genotoxic compounds may prove therapeutically important. One class of non-genotoxic p53 activators is known as the tenovins and exemplary compounds of this class are disclosed in WO 2008/029096 and by Lain, S. et al. (*Cancer Cell*, 2008, 13, 1-10).

One method of activating p53 is to inhibit its deacetylation by a group of NAD$^+$-dependent protein deacetylases known as the sirtuins (HDAC class III) (Lain, S. et al. infra)). To date, one sirtuin family member SIRT1 is known to regulate p53 activity by deacetylating p53 at Lys382 (Vaziri H, Dessain S K. Ng Eaton E. Imai S I. Frye R A. Pandita T K. Guarente L. Weinberg R A, *Cell*, 2001 107(2): 149-59; and Luo J. Nikolaev A Y. Imai S. Chen D. Su F. Shiloh A. Guarentre L. Gue W., *Cell*, 2001 107(2):137-48). Partly due to its ability to decrease p53 function, inhibiting SIRT1 is believed to represent an important target for cancer treatment (Lain, S. et al. (infra), Heltweg, B. et al. *Cancer Res.*, 2006 66(8), 4368-4377 and US 2005/0079995).

SIRT2, another of the sirtuins, is comparatively little studied vis-à-vis SIRT1 although, significantly, its inhibition has been linked with treatment for Parkinson's disease and other neurodegenerative disorders (Outeiro T F, Kontopoulos E, Altmann S M, Kufareva I, Strathearn K E, Amore A M, Volk C B, Maxwell M M, Rochet J C, McLean P J, Young A B, Abagyan R, Feany M B, Hyman B T, Kazantsev A G. Sirtuin 2 inhibitors rescue alpha-synuclein-mediated toxicity in models of Parkinson's disease. Science. 2007 Jul. 27; 317 (5837):516-9). Additionally, inhibition of other sirtuins, particularly SIRT2, as well as SIRT1, are thought to represent an important target for p53 activation and thus cancer therapy (Smith et al., *TRENDS in Cell* Biology, 2002, 12(9), 404-406. Moreover, Yun-Hye, J. et al. (*Biochem. Biophys. Res. Commun.*, 2008, 368, 690-695) report that SIRT2 interacts with various of the seven isoforms of 14-3-3 proteins, which are highly conserved in nature, including mammals and expressed in a wide range of tissue types and believed to play critical roles in various cellular mechanisms. It is also reported in this publication that SIRT2, like SIRT1, deacetylates p53, and down-regulates the transcriptional activity of p53. The inhibitory effect of SIRT2 on p53 is described as enhanced by the β and γ isoforms of 14-3-3. Accordingly, in addition to being useful in the treatment of neurodegenerative diseases such as Parkinson's; it is reasonable to postulate that inhibitors of SIRT2, like inhibitors of SIRT1, will allow the development of treatments for diseases associated with abnormalities or deficiencies with the p53 pathway including cancers and other hyperproliferative disorders.

Heltweg, B. et al. (*Cancer Res.*, 2006 66(8), 4368-4377 and US 2005/0079995) describe a compound called cambinol, and related analogues that are related to splitomicin, identified in a yeast-cell based screen for inhibitors of Sirp2 (Bedalov, A., *Proc. Natl. Acad. Sc: USA.*, 2001, 98, 15113-8).

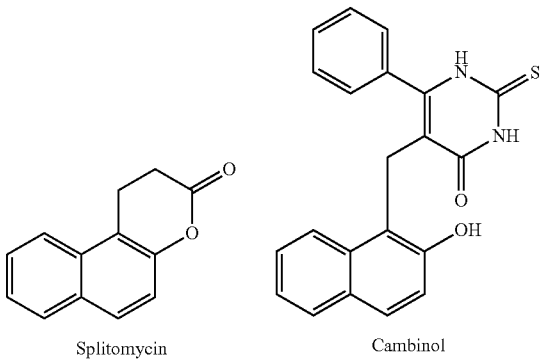 [SMILES: O=C1CCc2c(ccc3ccccc23)O1 ; O=c1[nH]c(=S)[nH]c(-c2ccccc2)c1Cc1c(O)ccc2ccccc12]

Splitomycin      Cambinol

Cambinol, the first sirtuin inhibitor with reported in vivo activity (Burkitt lymphoma-derived xenografts), inhibits SIRT1 and SIRT2 in vitro with IC$_{50}$ values of 56 and 59 μM respectively demonstrating moderate potency and no selectivity. Heltweg et al. describe only a very limited class of compounds related to the parent compound cambinol. Notably, there is no description of the change in the activity of the resultant compounds by incorporating substituents onto the phenyl ring of cambinol, or of including substituents in place of the N-1 and N-3 nitrogens' hydrogen atoms.

We have surprisingly found that significant, changes may be made to the structure of cambinol whereby to afford compounds having improved inhibitory activity over cambinol itself and/or selectivity towards either SIRT1 or SIRT2.

SUMMARY OF THE INVENTION

Viewed from a first aspect, therefore, the invention provides a compound according to formula (I):

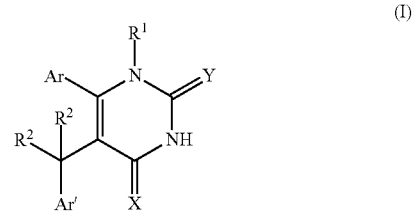

wherein:
X is O or S;
Y is O or S;
each Ar and Ar' is independently a mono-, bi- or tricyclic aryl or heteroaryl group optionally substituted with one or more substituents selected from halo, alkyl, aryl, heteroaryl, hydroxyl, nitro, amino, alkoxy, alkylthio, cyano, thio, ester, acyl and amido;

each $R^2$ is independently hydrogen, halo, alkyl, aryl, heteroaryl, hydroxyl, nitro, amino, alkoxy, alkylthio, cyano and thio; and $R^1$ is a straight-chain or branched $C_{1-25}$ alkyl group optionally interrupted (i) by replacing one or more of any of the carbon atoms of the alkyl group independently with one of the following diradical moieties: —O—, —S—, —N($R^6$)—, —C(=O)—, —SO$_2$N$R^6$—, —S(O)—, S(O)$_2$—, C(=O)N($R^6$)—, —C(=O)O—, —C(=S)—, —C(=S)O—, —C(=S)S—, —C(=O)S—, —C(=N—OH)—, —C(=N—O$R^6$)—, —C(=N$R^6$)—, —C(=N—NH$_2$)—, —C(=N—NH$R^6$)—, —C(=O)N($R^6$)C(=O)—, —C(=S)N($R^6$)C(=S)—, —C(=O)N($R^6$)C(=S)— and —C(=N—N($R^6$)$_2$)—, wherein $R^6$ is hydrogen or alkyl, and/or (ii) by replacing, of the six carbon atoms of the alkyl group nearest the nitrogen atom to which the alkyl group is attached, either two of these carbon atoms that are adjacent by a 1,2-disubstituted $C_{3-10}$ cycloalkylene, phenylene or monocyclic heteroarylene diradical, or three of these carbon atoms that are adjacent by a 1,3-disubstituted $C_{4-10}$ cycloalkylene, phenylene or monocyclic heteroarylene diradical, or four of these carbon atoms that are adjacent by a 1,4-disubstituted $C_{5-10}$ cycloalkylene, phenylene or monocyclic six-membered ring heteroarylene diradical, wherein any cycloalkylene, phenylene or monocyclic heteroarylene group present may be optionally substituted with one or more substituents selected independently from halo, hydroxyl, nitro, amino, cyano and thio; and wherein one or more of the hydrogen atoms of the alkyl group may be optionally substituted with one or more substituents selected independently from halo, hydroxyl, nitro, amino, cyano and thio, or a physiologically acceptable salt, solvate, ester, amide or other physiologically functional derivative thereof.

Viewed from a second aspect, the invention provides a compound according to formula (II):

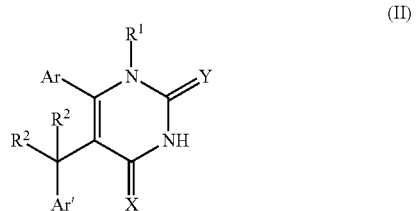

(II)

wherein:
X is O or S;
Y is O or S;
Ar— is

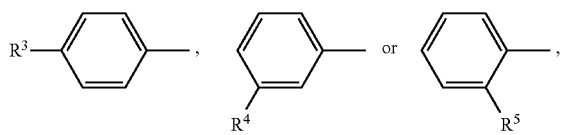

wherein $R^3$ is bromo, fluoro, or alkyl, $R^4$ is fluoro or alkyl and $R^5$ is fluoro or alkyl; Ar' is independently a mono-, bi- or tricyclic aryl or heteroaryl group optionally substituted with one or more substituents selected from halo, alkyl, aryl, heteroaryl, hydroxyl, nitro, amino, alkoxy, alkylthio, cyano, thio, ester, acyl and amido; each $R^2$ is independently hydrogen, halo, alkyl, aryl, heteroaryl, hydroxyl, nitro, amino, alkoxy, alkylthio, cyano and thio; and $R^1$ is hydrogen or a straight-chain or branched $C_{1-25}$ alkyl group wherein the alkyl group may be optionally interrupted (i) by replacing one or more of any of the carbon atoms of the alkyl group independently with one of the following diradical moieties: —O—, —S—, —N($R^6$)—, —C(=O)—, —SO$_2$N$R^6$—, —S(O)—, S(O)$_2$—, C(=O)N($R^6$)—, —C(=O)O—, —C(=S)—, —C(=S)O—, —C(=S)S—, —C(=O)S—, —C(=N—OH)—, —C(=N—O$R^6$)—, —C(=N$R^6$)—, —C(=N—NH$_2$)—, —C(=N—NH$R^6$)—, —C(=O)N($R^6$)C(=O)—, —C(=S)N($R^6$)C(=S)—, —C(=O)N($R^6$)C(=S)— and —C(=N—N($R^6$)$_2$)—, wherein $R^6$ is hydrogen or alkyl, and/or (ii) by replacing, of the six carbon atoms of the alkyl group nearest the nitrogen atom to which the alkyl group is attached, either two of these carbon atoms that are adjacent by a 1,2-disubstituted $C_{3-10}$ cycloalkylene, phenylene or monocyclic heteroarylene diradical, or three of these carbon atoms that are adjacent by a 1,3-disubstituted $C_{4-10}$ cycloalkylene, phenylene or monocyclic heteroarylene diradical, or four of these carbon atoms that are adjacent by a 1,4-disubstituted $C_{5-10}$ cycloalkylene, phenylene or monocyclic six-membered ring heteroarylene diradical, wherein any cycloalkylene, phenylene or monocyclic heteroarylene group present may be optionally substituted with one or more substituents selected independently from halo, hydroxyl, nitro, amino, cyano and thio; and wherein one or more of the hydrogen atoms of the alkyl group may be optionally substituted with one or more substituents selected independently from halo, hydroxyl, nitro, amino, cyano and thio, or a physiologically acceptable salt, solvate, ester, amide or other physiologically functional derivative thereof.

Viewed from a third aspect, the invention provides a compound of the first or second aspect in any one preceding claim, or physiologically acceptable salt, solvate, ester, amide or other physiologically functional derivative thereof, for use in medicine.

Viewed from a fourth aspect, the invention provides a compound of the first or second aspect, or physiologically acceptable salt, solvate, ester, amide or other physiologically functional derivative thereof, together with a pharmaceutically acceptable carrier.

Viewed from a further aspect, the invention provides a compound of the invention, or physiologically acceptable salt, solvate, ester, amide or other physiologically functional derivative thereof, for the treatment or prophylaxis of a disease involving cell proliferation, in particular cancer.

Viewed from a further aspect, the invention provides a compound of the invention or physiologically acceptable salt, solvate, ester, amide or other physiologically functional derivative thereof, for the treatment or prophylaxis of a disease involving associated with SirT1 or SirT2 expression and/or function.

Viewed from a further aspect, the invention provides a method of treatment or prophylaxis of a disease involving cell proliferation, in particular cancer, said method comprising administering a therapeutically or prophylactically useful amount of a compound of the invention, or physiologically acceptable salt, solvate, ester, amide or other physiologically functional derivative thereof, to a subject in need thereof.

Viewed from a further aspect, the invention provides a method of treatment or prophylaxis of a disease/condition associated with SirT1 or SirT2 expression and/or function said method comprising administering a therapeutically or prophylactically useful amount of a compound of the invention, or physiologically acceptable salt, solvate, ester, amide or other physiologically functional derivative thereof, to a subject in need thereof.

Viewed from a further aspect, the invention provides a method of treatment or prophylaxis of a disease/condition selected from the group consisting of diabetes, muscle differentiation, inflammation, aberrant or undesirable immune response, obesity, heart failure, neurodegeneration, aging, HIV infection or malaria, said method comprising administering a therapeutically or prophylactically useful amount of a compound of the invention, or physiologically acceptable salt, solvate, ester, amide or other physiologically functional derivative thereof, to a subject in need thereof.

Viewed from a further aspect, the invention provides use of a compound of the invention, or physiologically acceptable salt, solvate, ester, amide or other physiologically functional derivative thereof, in the manufacture of a medicament for use in any method of treatment or prophylaxis as defined herein.

Other aspects and embodiments of the invention will be evident from the discussion that follows.

DETAILED DESCRIPTION OF THE INVENTION

Figure 1:
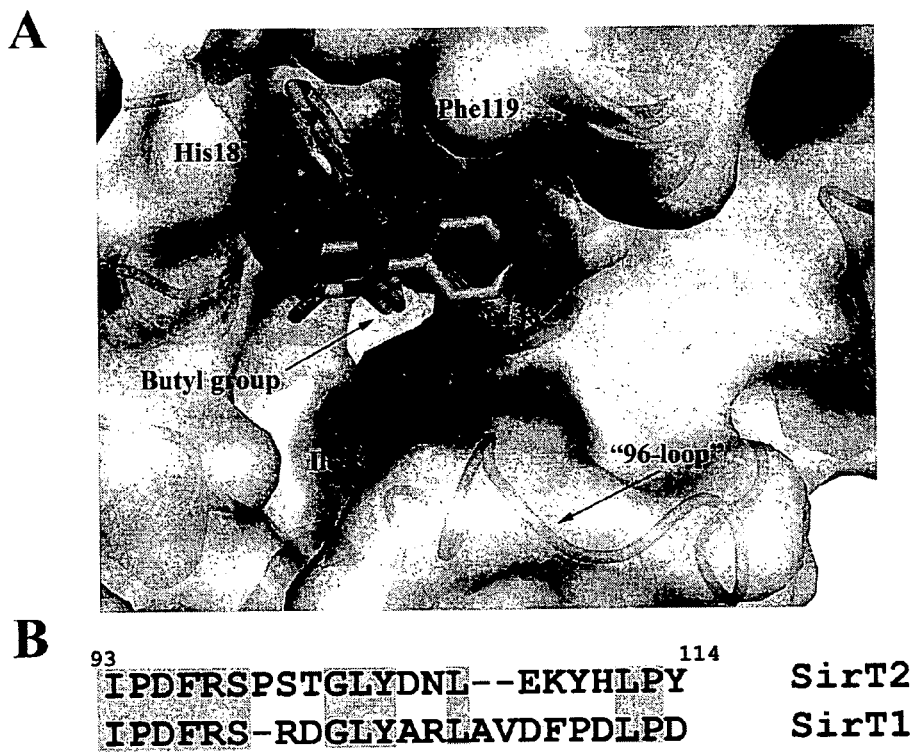
FIG. 1 shows a computer model of a compound of the invention bound in the nicotinamide C-sub pocket of the catalytic domain of SIRT2.

The present invention arises from the recognition that the compounds described herein possess surprisingly improved inhibitory effects against SIRT1 and/or SIRT2. Moreover the compounds are structurally surprising in the light of the teachings in the prior art. These features manifest themselves both in the data and studies reported herein and the fact that both Heltweg et al. (infra) and US 2005/00079995 ascribe utility only to cambinol itself of the pyrimidinones described in these publications.

The compounds of and utilised in the various aspects of the present invention of formulae (I) and (II) are based upon a central six-membered heterocyclic ring as depicted in these formulae. Firstly, the compounds of formula (I) are described.

Notable about the compounds of formula (I) vis-à-vis the prior art is the substitution of the N-1 atom with substituent $R^1$. This substituent is a straight-chain or branched $C_{1-25}$ alkyl group.

By alkyl is meant herein a saturated or unsaturated, but not aromatic, hydrocarbyl moiety, which may be straight-chain, cyclic or branched unless the context dictates to the contrary. The alkyl groups described herein may thus have one or more sites of unsaturation, which may be constituted by carbon-carbon double bonds or carbon-carbon triple bonds. Generally, the alkyl substituents described herein will be saturated alkyl radicals unless the context dictates to the contrary. Typically alkyl groups will comprise from 1 to 25 carbon atoms, more usually 1 to 10 carbon atoms, more usually still 1 to 6 carbon atoms.

Alkyl groups may be substituted and, the substituent may be comprised within the alkyl chain, referred to herein as interruption of the alkyl chain. Examples of such interruptions are substitutions with one of the following diradical moieties: —O—, —S—, —N($R^6$)—, —C(=O)—, —SO$_2$N$R^6$—, —S(O)—, S(O)$_2$—, C(=O)N($R^6$)—, —C(=O)O—, —C(=S)—, —C(=S)O—, —C(=S)S—, —C(=O)S—, —C(=N—OH)—, —C(=N—$OR^6$)—, —C(=N$R^6$)—, —C(=N—NH$_2$)—, —C(=N—NH$R^6$)—, —C(=O)N($R^6$)C(=O)—, —C(=S)N($R^6$)C(=S)—, —C(=O)N($R^6$)C(=S)— and —C(=N—N($R^6$)$_2$)—, wherein $R^6$ is hydrogen or alkyl. Alternatively, the substituent(s) may be pendant from the alkyl chain i.e. formally replacing one or more hydrogen atoms of the alkyl group. Examples of such substituents are halo (e.g. fluoro, chloro, bromo and iodo), hydroxyl, alkoxy, alkylthio, carboxy, thioacyl, acyl, nitro, thiol, cyano and the like.

By carboxy is meant herein the functional group $CO_2H$, which may be in deprotonated form ($CO_2^-$).

By acyl and thioacyl are meant the functional groups of formulae —C(O)-alkyl or —C(S)-alkyl respectively, where alkyl is as defined hereinbefore.

Alkyloxy (synonymous with alkoxy) and alkylthio moieties are of the formulae —O-alkyl and —S-alkyl respectively, where alkyl is as defined hereinbefore.

Alkyl groups $R^1$ herein are typically straight-chain, which, where interrupted, are interrupted so as not to extend the overall number of backbone atoms in the chain. This is achieved (formally) by replacing one or more of the carbon atoms in the alkyl group with one or more of the following diradical moieties described herein. Thus, for example, where the alkyl group is interrupted with an oxygen atom (whereby to form an ether) the alkyl group may have at most 24 carbon atoms in the chain; where the alkyl group is interrupted by a sulfonamide group (—SO$_2$N$R^6$) the backbone chain of the alkyl group may comprise at most 23 carbon atoms.

As an additional form of interruption in the alkyl group $R^1$, two or more adjacent carbon atoms proximate to the nitrogen atom to which alkyl group $R^1$ is attached may be replaced by a cycloalkylene, phenylene or monocyclic heteroarylene moiety whereby to interrupt the alkyl chain $R^1$ with a cyclic species. Where the alkyl group $R^1$ is interrupted in this way, such an interruption may be present once or twice, typically once, if such an interruption is indeed present, by replacing two or more of the six carbon atoms of the alkyl group nearest the nitrogen atom to which alkyl group $R^1$ is attached, more typically by replacing two or more of the four atoms of the alkyl group nearest the nitrogen atom to which alkyl group $R^1$ is attached.

As those skilled in the art are aware, cycloalkyl represents a cyclic alkyl group formed formally by abstraction of one hydrogen atom from a cycloalkyl. A cycloalkylene diradical is formed by abstraction of two hydrogen atoms. As with alkyl substituents, cycloalkylene moieties present may comprise one or more sites of interruption. These may comprise the same diradical moieties described hereinabove in connection with the definition of alkyl; more typically, any such interrupting moieties are selected from the group consisting of —O—, —S— and —N($R^6$)—, wherein $R^6$ is described hereinabove, and typically hydrogen. Generally, cycloalkylene moieties, if present in alkyl $R^1$, comprise no interrupting diradical as part of the cycloalkylene.

Alkyl group $R^1$ may alternatively or additionally comprise an interrupting phenylene or monocyclic heteroarylene diradical. Such diradicals are formally derived by abstraction of two hydrogen atoms from benzene and monocyclic heteroaromatic compounds respectively, or one hydrogen atom from a phenyl or monocyclic heteroaryl radical.

By aryl is meant herein both monocyclic aryl (i.e. phenyl) or polycyclic aryl radicals such as napthyl or anthracyl. Heteroaryl moieties are aromatic moieties that comprise one or more heteroatoms, typically O, N or S, in place of one or more carbon atoms and any hydrogen atoms attached thereto. Heteroaryl moieties may likewise be monocyclic (e.g. pyridyl, furyl, pyrrolyl and pyrimidinyl). An example of a polycyclic heteroaryl is indanyl. Typically the heteroatoms in any heteroaryl moieties present is or are oxygen or nitrogen.

If alkyl $R^1$ comprises a cycloalkylene, phenylene or monocyclic heteroarylene diradical, such a diradical may be optionally substituted with any substituents with which alkyl may be substituted as described herein. More typically such substituents where present are selected from halo, hydroxyl, nitro, amino, cyano and thio. Often, however, any such diradicals will be unsubstituted.

Where alkyl groups $R^1$ comprise one or more cyclic diradical moieties as a surrogate for two or more adjacent carbon atoms of the six, more typically four, carbon atoms closest to the nitrogen atom which $R^1$ is attached, the number of atoms of these diradicals interposed in the alkyl backbone replace a length of alkyl chain comprising the same number of carbon, heteroatom or interrupting atoms. Thus, for example, where the alkyl chain $R^1$ comprises a 1,2-disubstituted $C_{3-10}$ cycloalkylene, arylene, or monocyclic heteroarylene, in which the interrupting cyclic diradical connects to the alkyl chain through adjacent, and thus two, atoms, such diradicals may take the place of two adjacent of the six (more typically four) carbon atoms of the alkyl group $R^1$ that are closest to the nitrogen atom to which $R^1$ is attached.

Analogously, where a 1,3-disubstituted $C_{4-10}$ cycloalkylene, phenylene or monocyclic heteroarylene diradical is present, such an interrupting diradical may be considered to insert three atoms into the length of the alkyl group $R^1$ and so may be understood to replace three of the carbon atoms of the alkyl group.

Finally, where a 1,4-disubstituted $C_{5-10}$ cycloalkylene, phenylene or monocyclic 6-membered ring heteroarylene diradical is present, this may replace four of the carbon atoms the alkyl group $R^1$.

Typically at most one interrupting cyclic diradical will be present in alkyl group $R^1$. In many embodiments of the invention no cyclic diradical moieties will be present.

Without wishing to be bound by theory, by strictly defining the location within the alkyl group $R^1$ where optionally interrupting cyclic diradicals may be present, the location of any such diradicals is confined to the end of the alkyl group $R^1$ most proximate to the mouth of what appears to be a comparatively narrow lipophilic channel in which the alkyl group $R^1$ is believed to be bound.

Moiety Ar in compounds of formula (I) may be a mono-, bi-, or tricyclic aryl or heteroaryl group optionally substituted with one or more substituents selected from halo, alkyl, aryl, heteroaryl, hydroxyl, nitro, amino, alkoxy, alkylthio, cyano, thio, ester, acyl and amido. Typically, Ar in compounds of formula (I) is a monocyclic aryl or heteroaryl group, more typically still a phenyl group. In certain embodiments of compounds of formula (I) Ar is unsubstituted.

An ester comprises a unit of the formula —C(O)O— and may be flanked by straight-chain, branched or cyclic alkyl, aryl or heteroaryl moieties. Thus, for example, where an aryl group is substituted with an ester moiety, this may be connected to the aryl group through either the oxygen and carbonyl carbons thereof. Similarly, amido (—(NR$^6$)C(O)—) and sulfonamide (—SO$_2$N(R$^6$)—) groups, wherein R$^6$ is as hereinbefore defined, typically hydrogen, may be attached to an aryl group, for example, by either the carbon and/or oxygen atoms (with amido groups) or sulfur and/or nitrogen atoms (with sulfonamide groups).

Unless the context dictates to the contrary, an amino group is of the formula N(R$^6$)$_2$ or NR$^6$ as the valency of the atom(s) to which the nitrogen atom is attached allow(s), wherein (each) R$^6$ is selected (independently) from the group R$^6$ as hereinbefore defined.

References to amino or amine herein, where the context permits, embrace cyclic amino groups, i.e. wherein the nitrogen atom of the amino group or amine is a member of a ring. References to amino or amine herein also include references to quaternised versions of amines, and salts thereof. For example, an amine may be protonated and form a salt with a number of acids, such as hydrochloric acid or sulfuric acid, including carboxylic acids. The hydrochloride salts of an amine may advantageously exhibit increased solubility in water and aqueous solvents.

Each $R^2$ in compounds of formulae (I) may be independently selected from hydrogen, halo, alkyl, aryl, heteroaryl, hydroxyl, nitro, amino, alkoxy, alkylthio, acyl and thio. More typically these substituents are independently selected from hydrogen, halo, $C_{1-6}$ alkyl, more particularly $C_{1-6}$ saturated alkyl, still more particularly $C_{1-3}$ saturated alkyl, hydroxyl, nitro, amino (e.g. NH$_2$ or dimethylamino), $C_{1-6}$ alkoxy, alkylthio, cyano and thio, still more particularly hydrogen, halo, methyl, NH$_2$, $C_{1-3}$ alkoxy, and cyano and thio. In many embodiments of the invention both substituents $R^2$ will be hydrogen, or $C_{1-3}$ saturated alkyl, particularly hydrogen or methyl.

Moiety Ar' in compounds of the invention is a mono-, bi- or tricyclic aryl or heteroaryl group, more particularly a bicyclic aryl or heteroaryl group, for example a bicyclic aryl group. Alternatively, Ar' may comprise an aryl or a heteroaryl-substituted aryl or heteroaryl group, for example an aryl substituted phenyl group.

Typically Ar' is substituted although it may be unsubstituted. Where substituted, typically between 1 and 5, e.g. between 1 and 3, substituents are present. Typically at least one of the substituents with which Ar' is substituted is an amino (generally NH$_2$), hydroxyl or thiol group. In certain embodiments of the invention Ar' is substituted only with an amino (typically NH$_2$), hydroxyl or thiol group. Typically, an amino (NH$_2$), hydroxyl or thiol group is present on an atom (normally a carbon atom) adjacent to the atom of Ar' connected to the remainder of the compound of the invention. Most typically, Ar' is an optionally substituted β-naphthyl moiety. In certain embodiments of the invention Ar' is an unsubstituted β-naphthyl group.

X and Y may be independently oxygen or sulfur. Typically X is oxygen. Typically Y is sulfur. However the invention is not to be understood to be so limited.

The compounds according to formula (II) will now be described.

In compounds of formula (II) $R^1$, $R^2$, $R^7$, X, Y and Ar' may each be as described herein in connection with the compounds of formula (I) with the additional possibility that alkyl group $R^1$ may be hydrogen.

In the compounds of formula (II), Ar' may be a para bromo, fluoro or alkyl group; a meta fluoro or alkyl group; or an ortho fluoro or alkyl group. In some nomenclature employed herein, where a substituent is on the phenyl group Ar in compounds of formula (II), this is referred to as R'. In certain embodiments of the invention, compounds of formula (II) comprise a substituted or unsubstituted alkyl group, generally an unsubstituted alkyl group. Typically the alkyl group will be a saturated alkyl group, for example a saturated unsubstituted alkyl group. Particularly typically, where substituent $R^3$, $R^4$ or $R^5$ is an alkyl group, this is a $C_{1-6}$-unsubstituted, saturated alkyl group such as methyl, ethyl, propyl etc. Where $R^3$, $R^4$ or $R^5$ (or any other alkyl group described herein, unless the context dictates to the contrary) is an unsubstituted, saturated alkyl group comprising three or more carbon items, it will be understood that this may be a straight-chain, branched or cyclic alkyl group, for example n-propyl, iso-propyl or cyclopropyl etc. Typically, where $R^3$, $R^4$ or $R^5$ is an alkyl group, this is a methyl, ethyl or propyl group, particularly a methyl or ethyl group, still more particularly a methyl group.

In particular embodiments of the invention, compounds of formula (II) comprise a para bromo phenyl moiety as Ar'.

It will be understood that the invention also comprises compounds of formula (I) comprising Ar groups that are $R^3$, $R^4$ and $R^5$-substituted phenyl rings as particularly described in connection with compounds of formula (II) but which Ar groups are not limited to presence in compounds of formula (II).

The compounds of the present invention may be used for the treatment and/or prophylaxis of conditions and diseases involving abnormal cell death associated with abnormalities with the p53 protein, its function and/or the p53 pathway.

In particular, diseases involving abnormal proliferation of cells are treatable with the compounds recited herein. Examples of such diseases include cancers, hyperproliferative disorders (including warts, psoriasis, inflammatory bowel disease), rheumatoid/autoimmune conditions, sickle cell anemia and thalasemias.

In addition the compounds of the present invention are of use in the treatment and/or prophylaxis of conditions and diseases associated with sirtuin expression and/or function, in particular expression and/or function of SirT1 of SirT2, such as cancer, diabetes muscle differentiation, heart failure, neurodegenerative disorders such as Parkinson's disease, aging, HIV infection and malaria.

The compounds of the present invention are also effective at inhibiting sirtuin activity, in particular SIRT1 and/or SIRT2 activity. Thus compounds of the present invention may be of use in treating diseases/conditions associated with expression or functioning of sirtuins in particular SIRT1 and SIRT2.

SirT1 and related proteins, including other members of the Sir2 family of enzymes, have been identified as being a target in a great many diseases/conditions, including cancer, ageing, diabetes, muscle differentiation, heart failure, neurodegeneration, HIV infection and malaria (see for example, Bordone L, Guarente L., *Cancer Res.* 2006 Apr. 15; 66(8):4368-77; Heltweg et al. *Trends Pharmacol Sci.* 2005 February; 26(2): 94-103; Pagans et al.; *PLoS Biology* 2005 Vol. 3, No. 2, e41; Deitsch K W, Cell. 2005 Apr. 8; 121(1):1-2; Freitas-Junior L H et al, Cell. 2005 Apr. 8; 121(1):25-36, Nayagam V M, *J. Biomol. Screen.* 2006 Nov. 12). Accordingly, the compounds of the present invention may find utility in treating/preventing any of these diseases/conditions.

As described hereinbefore, inhibition of SirT2, in addition to allowing the treatment or prophylaxis of neurodegenerative diseases including Parkinson's disease, also allows treatment or prophylaxis of diseases involving abnormal proliferation of cells. Examples of such diseases include cancers, hyperproliferative disorders (including warts, psoriasis, inflammatory bowel disease), rheumatoid/autoimmune conditions, sickle cell anaemia, thalasemias and the like. Cancers include the cancers described hereinbefore. Thus the compounds of the present invention, particularly of formula (I), are useful in the treatment of prophylaxis of such conditions. Compounds of formula (II) are also useful in the treatment or prophylaxis of diseases including cancer, inflammation, immune response, obesity, ageing, diabetes, muscle differentiation, heart failure, neurodegeneration, HIV infection and malaria.

In certain embodiments of the invention, therefore the compounds are used for the treatment or prophylaxis of cancer.

Examples of cancers which may be treated include, but are not limited to, a carcinoma, for example a carcinoma of the bladder, breast, colon (e.g. colorectal carcinomas such as colon adenocarcinoma and colon adenoma), kidney, epidermal, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, prostate, or skin, for example squamous cell carcinoma; a hematopoietic tumour of lymphoid lineage, for example leukaemia, acute lymphocytic leukaemia, B-cell lymphoma, T-cell lymphoma, Hodgkin's lymphoma, non-Hodgkin's lymphoma, hairy cell lymphoma, or Burkett's lymphoma; a hematopoietic tumour of myeloid lineage, for example acute and chronic myelogenous leukaemia's, myelodysplastic syndrome, or promyelocytic leukaemia; thyroid follicular cancer; a tumour of mesenchymal origin, for example fibrosarcoma or habdomyosarcoma; a tumour of the central or peripheral nervous system, for example astrocytoma, neuroblastoma, glioma or schwannoma; melanoma; seminoma; teratocarcinoma; osteosarcoma; xenoderoma pigmentosum; keratoctanthoma; thyroid follicular cancer; or Kaposi's sarcoma.

Other therapeutic agents (e.g. antineoplastic agents) may be administered together (whether concurrently or at different time intervals) with the compounds of the formula (I). Examples of such other therapeutic agents include but are not limited to topoisomerase inhibitors, alkylating agents, antimetabolites, DNA binders and microtubule inhibitors (tubulin target agents), such as cisplatin, cyclophosphamide, doxorubicin, etoposide, irinotecan, fludarabine, 5FU, taxanes or mitomycin C. Other therapeutic agents will be evident to those skilled in the art. For the case of active compounds combined with other therapies the two or more treatments may be given in individually varying dose schedules and via different routes.

The combination of the agents listed above with a compound of the present invention would be at the discretion of the physician who would select dosages using his common general knowledge and dosing regimens known to a skilled practitioner.

Where a compound of the invention is administered in combination therapy with one, two, three, four or more, preferably one or two, preferably one other therapeutic agents, the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer period apart where required), the precise dosage regimen being commensurate with the properties of the therapeutic agent(s).

The compounds of the invention may also be administered in conjunction with non-chemotherapeutic treatments such as radiotherapy, photodynamic therapy, gene therapy; surgery and controlled diets.

The patient is typically an animal, e.g. a mammal, especially a human.

By a therapeutically or prophylactically effective amount is meant one capable of achieving the desired response, and will be adjudged, typically, by a medical practitioner. The amount required will depend upon one or more of at least the active compound(s) concerned, the patient, the condition it is desired to treat or prevent and the formulation of order of from 1 μg to 1 g of compound per kg of body weight of the patient being treated.

Different dosing regiments may likewise be administered, again typically at the discretion of the medical practitioner. As alluded to hereinafter the low toxicity of the compounds of the invention, allow for at least daily administration although regimes where the compound(s) is (or are) administered more infrequently, e.g. every other day, weekly or fortnightly, for example, are also embraced by the present invention.

By treatment is meant herein at least an amelioration of a condition suffered by a patient; the treatment need not be curative (i.e. resulting in obviation of the condition). Analogously references herein to prevention or prophylaxis herein do not indicate or require complete prevention of a condition; its manifestation may instead be reduced or delayed via prophylaxis or prevention according to the present invention.

For use according to the present invention, the compounds or physiologically acceptable salt, solvate, ester or other physiologically acceptable functional derivative thereof described herein may be presented as a pharmaceutical formulation, comprising the compound or physiologically acceptable salt, ester or other physiologically functional derivative thereof, together with one or more pharmaceutically acceptable carriers therefor and optionally other therapeutic and/or prophylactic ingredients. Any carrier(s) are acceptable in the sense of being compatible with the other ingredients of the formulation and not deleterious to the recipient thereof.

Examples of physiologically acceptable salts of the compounds according to the invention include acid addition salts formed with organic carboxylic acids such as acetic, lactic, tartaric, maleic, citric, pyruvic, oxalic, fumaric, oxaloacetic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids.

Physiologically functional derivatives of compounds of the present invention are derivatives, which can be converted in the body into the parent compound. Such physiologically functional derivatives may also be referred to as "pro-drugs" or "bioprecursors". Physiologically functional derivatives of compounds of the present invention include hydrolysable esters or amides, particularly esters, in vivo. Determination of suitable physiologically acceptable esters and amides is well within the skills of those skilled in the art.

It may be convenient or desirable to prepare, purify, and/or handle a corresponding solvate of the compounds described herein, which may be used in the any one of the uses/methods described. The term solvate is used herein to refer to a complex of solute, such as a compound or salt of the compound, and a solvent. If the solvent is water, the solvate may be termed a hydrate, for example a mono-hydrate, di-hydrate, tri-hydrate etc, depending on the number of water molecules present per molecule of substrate.

It will be appreciated that the compounds of the present invention may exist in various stereoisomeric forms and the compounds of the present invention as hereinbefore defined include all stereoisomeric forms and mixtures thereof, including enantiomers and racemic mixtures. The present invention includes within its scope the use of any such stereoisomeric form or mixture of stereoisomers, including the individual enantiomers of the compounds of formulae (I) or (II) as well as wholly or partially racemic mixtures of such enantiomers.

The compounds of the present invention may be prepared using reagents and techniques readily available in the art and/or exemplary methods as described hereinafter.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. Methods typically include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release-controlling matrix, or is coated with a suitable release-controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds.

Pharmaceutical formulations suitable for parenteral administration include sterile solutions or suspensions of an active compound in aqueous or oleaginous vehicles.

Injectible preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microliters, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

It should be understood that in addition to the aforementioned carrier ingredients the pharmaceutical formulations described above may include, an appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

Pharmaceutically acceptable carriers are well known to those skilled in the art and include, but are not limited to, 0.1 M and preferably 0.05 M phosphate buffer or 0.8% saline. Additionally, pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

Therapeutic formulations for veterinary use may conveniently be in either powder or liquid concentrate form. In accordance with standard veterinary formulation practice, conventional water soluble excipients, such as lactose or sucrose, may be incorporated in the powders to improve their physical properties. Thus particularly suitable powders of this invention comprise 50 to 100% w/w and preferably 60 to 80% w/w of the active ingredient(s) and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain the compound or a derivative or salt thereof and may optionally include a veterinarily acceptable water-miscible solvent, for example polyethylene glycol, propylene glycol, glycerol, glycerol formal or such a solvent mixed with up to 30% v/v of ethanol. The liquid concentrates may be administered to the drinking water of animals.

The invention is now described by the following non-limiting examples:

Synthesis of Cambinol and its Analogs

An authentic sample of cambinol (1) was prepared using a previously reported route, (Whamhoff, H.; Korte, F. Heterocycles by capture reactions of opened acyllactones. IV. A simple synthesis of 5H-[1]benzopyrano and 12H-naphtho[1', 2':5',6']pyrano[2,3-d]pyrimidines. *Chem. Ber.* 1967, 100, 1324-1330.) in 42% yield over 3 steps accordingly to Scheme 1.

Scheme 1: Synthetic route to Cambinol (1) and its analogs

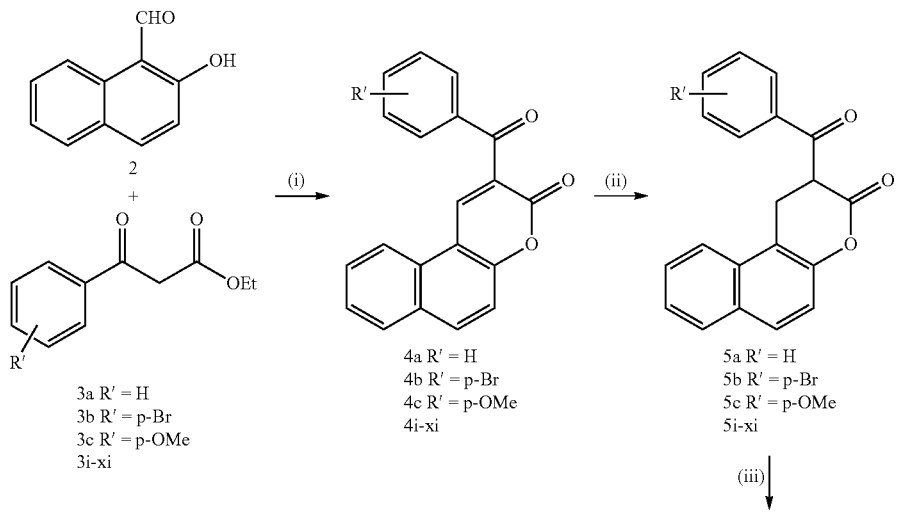

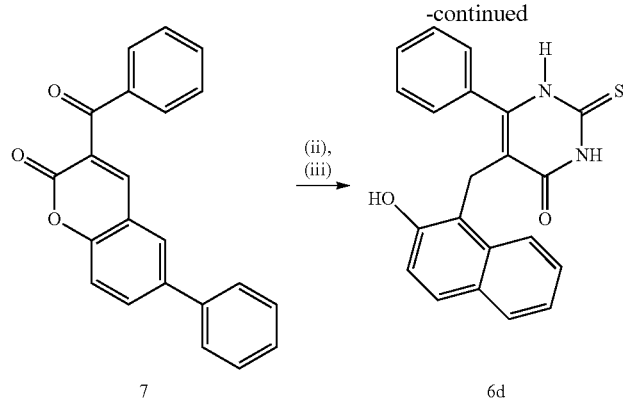
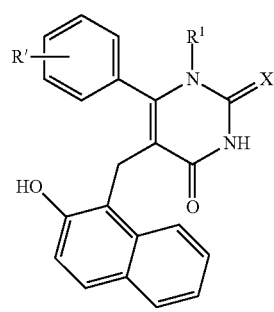

1 R' = R¹ = H, X = S, Cambinol
6a R' = R¹ = H, X = O
6b R' = p-Br, R¹ = H, X = S
6c R' = p-OMe, R¹ = H, X = S
6e R' = H, R¹ = Me, X = S
6i-xi R¹ = H, X = S
6f, g, h, j R' = H, X = S, R¹ varies Reagents and conditions: i) Piperidine, Ethanol, reflux, 2 h., for 4a, 86%; 4b, 87%; 4c, 95%; ii) NaBH$_4$, Pyridine, rt, 2 h., 5a, 95%; 5b, 93%; 5c, 76%; 7 was reduced in 95%; iii) Na, Ethanol, thiourea (for 1, 51%; 6b, 43%; 6c, 42%; 6d, 40%) or urea (6a, 20%) or N-methyl-thiourea (6e, 16%), reflux, 18 h. For substituents in compound i-xi see Table of testing data below Summary Initial Knoevenagel condensation of 2-hydroxy-1-naphthaldehyde (2) with ethyl benzoylacetate (3a) afforded 3-benzoyl-5,6-benzocoumarin (4a). Subsequent conjugate reduction of 4a using sodium borohydride in pyridine (Kadin, S. B. Reduction of conjugated double bonds with sodium borohydride. *J. Org. Chem.* 1966, 31, 620-622.) gave the saturated lactone 5a that was then converted on treatment with excess thiourea in the presence of sodium ethoxide to 1. An analogous approach was used to prepare a set of cambinol analogs in which i) the thiocarbonyl group in 1 was replaced by a carbonyl group (6a); ii) electron-withdrawing (e.g. bromine in 6b) or electron-donating (e.g. methoxy in 6c) substituents were incorporated in the para-position of the phenyl ring in 1; iii) the β-naphthol ring in 1 was replaced by a biphenyl-4-ol group (6d) and iv) a methyl group ($R_1$=Me, 6e) was incorporated at the N-1 position in 1. In brief, replacement of thiourea with urea enabled the conversion of 5a to 6a and analogs 6b and 6c were prepared from the corresponding commercially available ethyl benzoylacetates 3b and 3c respectively. In order to prepare analog 6d, 3-benzoyl-6-phenyl-chroman-2-one (7) (Scheme 1) was synthesised from 5-bromo-2-hydroxy-benzaldehyde in 55% yield over 2 steps. Conversion of 7 to the desired analog 6d was carried out by conjugate reduction and subsequent reaction with thiourea in the presence of base.

General Procedure for Preparation of 4a-4c:

Ethyl benzoyl acetate analog 3 (1.06 g, 5 mmol) was added to a warm solution of 2-hydroxy-1-naphthaldehyde (2) (0.86 g, 5 mmol) in ethanol (10 mL). Piperidine (15 drops) was added and the reaction was refluxed for 2 h. After cooling down, the product was collected by filtration, washed with ethanol and recrystallized from ethanol.

2-Benzoyl-benzo[f]chromen-3-one (4a)

Yielded 1.30 g (4.33 mmol, 86%) as a yellow powder. m. p. 208-210° C. (lit.m.p. 209° C.). ¹H NMR (CDCl$_3$, 300 MHz): δ=8.93 (s, 1H, 1-H), 8.27 (d, 1H, J=8.2 Hz, 10-H), 8.12 (d, 1H, J=9.0 Hz, 6-H), 7.98-7.90 (m, 3H, 10-H+2×Ph), 7.73 (ddd, 1H, ³J=7.0 Hz, ⁴J=1.2 Hz, 9-H), 7.67-7.59 (m, 2H, 8-H+1×Ph), 7.56-7.47 (m, 3H, 5-H+2×Ph).

2-(5'-Bromo-benzoyl)-benzo[f]chromen-3-one (4b)

m.p. 245-248° C. (lit. 246-247° C.). ¹H NMR (CDCl$_3$, 400 MHz): δ=8.98 (s, 1H, H-1), 8.29 (d, 1H, J=8.3 Hz, H-10), 8.13 (d, 1H, J=9.0 Hz, H-6), 7.96 (d, 1H, J=8.2 Hz, H-7), 7.81-7.73 (m, 3H, H-9, 2×ArH, AA'BB' system, J=8.7 Hz, H-3', H-7'), 7.64 (m, 3H, H-8, 2×ArH, AA'BB' system, J=8.7 Hz, H-4', H-6'), 7.51 (d, 1H, J=9.0 Hz, H-5). LR MS [ES⁺]: m/z 401.07 [M+Na]⁺(100%).

2-(4-Methoxy-benzoyl)-benzo[f]chromen-3-one (4c)

Yielded 1.45 g (4.39 mmol, 95%) as a white-red powder. m. p.: 207-210° C. (lit.m.p. 209-210° C.). ¹H NMR (400 MHz, CDCl$_3$): δ=8.86 (s, 1H, 1-H), 8.26 (d, 1H, J=8.4 Hz, 10-H), 8.10 (d, 1H, J=9.0 Hz, 6-H), 7.98-7.89 (m, 3H, 7-H+2×Ph, AA'BB' system, J=8.8 Hz, 3'-H, 7'-H), 7.72 (ddd, 1H, ³J=7.1, ⁴J=1.2 Hz, 9-H), 7.61 (ddd, 1H, ³H=7.1, ⁴J=1.0 Hz, 8-H), 7.53 (d, 1H, J=9.0 Hz, 5-H), 6.97 (d, 2H, AA'BB' system J=8.8 Hz, 4'-H, 6'-H), 3.83 (s, 3H, CH$_3$O).

General procedure for preparation of 3-benzoyl-5,6-benzo-3,4-diydrocoumarins 5a-5c NaBH$_4$ (59 mg, 1.56 mmol) was added to a stirring solution of 3-benzoyl-5,6-benzocoumarins (4) (500 mg, 1.56 mmol) in dry pyridine (10 mL). The reaction was stirred at room temperature for 3 h and checked by TLC. The reaction was poured into cold 2M hydrochloric acid (90 ml). The resulting white precipitate was collected by filtration, washed with ethanol and recrystallized from ethanol.

2-Benzoyl-1,2-dihydro-benzo[f]chromen-3-one (5a)

Yielded 440 mg (1.45 mmol, 95%) as a yellow powder. m. p. 158-160° C. (lit. m.p. 158-160° C.). ¹H NMR (CDCl$_3$, 300 MHz): δ=8.03-7.98 (m, 2H, Ph), 7.90-7.85 (m, 2H, 7-H, 10-H), 7.81 (d, 1H, J=9.0 Hz, 6-H), 7.63 (ddd, 1H, ³J=7.4 Hz, ⁴J=1.2 Hz, 9-H), 7.56 (ddd, 1H, ³J=6.7 Hz, ⁴J=1.1 Hz, 8-H), 7.54-7.45 (m, 3H, Ph), 7.29 (d, 1H, J=9.0 Hz, 5-H), 4.82 (dd, 1H, J=6.8 Hz, 2-H), 3.85 (dd, 1H, J=10.4 Hz, 1-H), 3.62 (dd, 1H, J=6.8 Hz, 1-H).

2-(5'-Bromo-benzoyl)-benzo[f]chromen-3-one (5b)

Yellow powder, yielded 892 mg (2.35 mmol, 94%). $^1$H NMR spectrum (CDCl$_3$, 400 MHz): 7.5 (d, 1H, J=9.0 Hz), 7.64 (m, 3H, AB system+ArH), 7.78 (m, 3H, AB system+ArH), 7.96 (d, 1H, J=8.2 Hz), 8.13 (d, 1H, J=9.1 Hz), 8.29 (d, 1H, J=8.3 Hz), 8.98 (s, 1H). LRMS (ES$^+$): m/z 401.05 [M+Na]$^+$(100%) and m/z 403.05 [M+Na]$^+$(93%).

2-(5'-Methoxy-benzoyl)-1,2-dihydro-benzo[f]chromen-3-one (5c)

Yielded 400 mg (1.20 mmol, 76%) as a white-red powder. m. p. 175-176. $^1$H NMR (400 MHz, CDCl$_3$): δ=7.99 (d, 2H, AA'BB' system, J=9.0 Hz, 3'-H, 7'-H), 7.90-7.84 (m, 2H, 10-H, 7-H), 7.80 (d, 1H, J=9.0 Hz, 6-H), 7.56 (ddd, 1H, $^3$J=7.0 Hz, $^4$J=1.0 Hz, 9-H), 7.47 (ddd, 1H, $^3$J=8.0 Hz, $^4$J=1.0 Hz, 8-H), 7.27 (d, 1H, J=9.0 Hz, overlapped with solvent signal, 5-H), 6.97 (d, 2H, J=9.0 Hz, AA'BB' system, J=9.0 Hz, 4'-H, 6'-H), 4.77 (dd, 1H, J=6.8 Hz, 2-H), 3.88 (s, 3H, CH$_3$O), 3.83 (dd, 1H, J=10.4 Hz, 1-H), 3.60 (dd, 1H, J=6.8 Hz, 1-H).

General Procedure for the Synthesis of Cambinol (1) and its Analogs 6b and 6c:

To a solution of NaOEt (2M) prepared dissolving Na metal into dry ethanol, thiourea (15.6 eq) and different 2-benzoyl-5,6-benzo-1,2-dihydrocoumarins (1 eq) were added and the reaction refluxed for 18 h. After removing the solvent in vacuo, the crude reaction mixture was dissolved in distilled water and the products precipitated after addition of 2M aqueous HCl. The solid was collected by filtration and purified by recrystallization from ethanol.

5-(2"-Hydroxy-naphthalen-1-ylmethyl)-6-phenyl-2-thioxo-2,3-dihydro-1H-pyrimidin-4-one (1, Cambinol)

Yielded 120 mg (51%) as a white powder after recrystallysation from ethanol. m. p. 253-255° C. IR (NaCl, thin layer) v$_{max}$cm$^{-1}$ 3111 (OH), 2804 (CH$_2$), 1628 (C=O), 1556 (NH), 1494 (C—N), 1212 (C=S, CSNH), 877 and 766 (C—H$_{Ar}$). $^1$H NMR (400 MHz, DMSO-d$_6$): δ=12.55 (br, 1H, NH), 12.30 (br, 1H, NH), 9.44 (s, 1H, OH), 7.64 (d, 1H, J=7.7 Hz, H-5"), 7.48 (d, 1H, J=8.8 Hz, H-4"), 7.44-7.11 (m, 8H, H-6", H-7", H-8"+5×ArH), 6.90 (d, 1H, J=8.8 Hz, H-3"), 3.90 (s, 2H, H). $^{13}$C NMR (100 MHz, DMSO-d$_6$): δ=173.8 (C=S), 162.2 (C=O), 152.7 (C2"), 150.1 (C6), 133.1 (C8"a), 131.6 (C1'), 129.4 (C4'), 128.5 (C5', C3'), 128.0 (C5"), 128.0 (C4"a), 127.8 (C2', C6'), 127.5 (C4"), 125.5 (C7"), 122.8 (C6"), 121.9 (C8"), 118.3 (C3"), 116.4 (C1"), 115.2 (C5), 21.5 (CH$_2$). LR MS [ES$^+$]: m/z 382.97 [M+Na]$^+$ (100%); LR MS [ES$^-$]: m/z 358.78 [M−H]$^-$ (100%); HR MS [ES$^-$]: m/z calc'd for C$_{21}$H$_{15}$N$_2$O$_2$S 359.0854 [M−H]$^-$. found 359.0858 (−0.9 ppm). A sample of 1 was further recrystallized from ethanol to give crystals of sufficient size for small molecule X-ray crystallographic analysis by slow evaporation from ethanol.

6-(4-Bromo-phenyl)-5-(2-hydroxy-naphthalen-1-ylmethyl)-2-thioxo-2,3-dihydro-1H-pyrimidin-4-one (6b)

Yielded 100 mg (0.22 mmol, 43%) as a white powder. mp 282-287 C°. IR (NaCl, thin layer) v$_{max}$: 3413 (OH), 1699 and 1634 C=O), 1547 (NH), 1445 (C—N), 1189 (C=S, CSNH), 1158, 1124 and 1112 (C—O and C=S), 1070 (C—O), 971, 827 and 742 (C—H$_{Ar}$), 668 (C—Br). $^1$H NMR (400 MHz, DMSO-d$_6$): δ=12.56 (br, 1H, NH), 12.22 (br, 1H, NH), 9.42 (s, 1H, OH), 7.71 (d, 1H, J=7.5 Hz, 5"-H), 7.47 (d, 1H, J=8.8 Hz, 4"-H), 7.44 (d, 1H, J=8.7 Hz, 4"-H), 7.32 (d, 2H, AA'BB' system, J=8.4 Hz, 2'-H, 6'-H), 7.26 (ddd, 1H, $^3$J=7.0 Hz, $^4$J=1.2 Hz, 7"-H), 7.17 (ddd, 1H, $^3$J=7.3 Hz, $^4$J=0.7 Hz, 6"-H), 6.98 (d, 2H, AA'BB' system, J=8.4 Hz, 3'-H, 5'-H), 6.87 (d, 1H, J=8.7 Hz, 3"-H), 3.91 (s, 2, CH$_2$). $^{13}$C NMR (100 MHz, DMSO-d$_6$): δ=173.8 (C=S), 161.9 (C=O), 152.6 (C2"), 148.8 (C6), 132.9 (C1'), 130.6 (C8"a), 130.4 (C3'), 130.1 (C2'), 128.0 (C5"), 127.9 (C4"a), 127.4 (C4"), 125.5 (C7"), 122.7 (C6"), 121.8 (C8"), 117.9 (C3"), 116.3 (C1"), 115.7 (C5), 20.9 (CH$_2$). LR MS [ES$^+$]: m/z 462.96 [M+Na]$^+$ (100%); LR MS [ES$^-$]: m/z 436.93 [M−H]$^-$ (100%); HR MS [ES−]: m/z calc'd for C$_{21}$H$_{12}$N$_2$O$_2$$^{81}$Br 436.9960 [M−H]$^-$. found 436.9970 (+0.2 ppm); m/z calc'd for C$_{21}$H$_{12}$N$_2$O$_2$$^{79}$Br 438.9945 [M−H]$^-$. found 438.9946 (+0.1 ppm).

5-(2-Hydroxy-naphthalen-1-ylmethyl)-6-(4-methoxy-phenyl)-2-thioxo-2,3-dihydro-1H-pyrimidin-4-one (6c)

Yielded 95 mg (0.24 mmol, 42%) as a white powder after recrystallisation from ethanol. mp 262-265 C°. IR (NaCl, thin layer) v$_{max}$: 3425 (OH), 2930 (CH2), 1652 and 1628 (C=O), 1576 (NH), 1457 (C—N), 1253 (OH), 1213, 1186 and 1023 (C—O and C=S), 736 (C—HAr). $^1$H NMR (400 MHz, DMSO-d$_6$): δ=12.52 (br, 1H, NH), 12.25 (br, 1H, NH), 9.50 (s, 1H, OH), 7.66 (ddd, 1H, $^3$J=7.7 Hz, $^4$J=1.3 Hz, 8"-H), 7.51 (d, 1H, J=8.8 Hz, 4"-H), 7.35 (d, 1H, J=8.3 Hz, 5"-H), 7.26-7.14 (m, 4H, 6'-H, 7'-H+2×Ph, AA'BB' system, J=8.7 Hz, 2'-H, 6'-H), 6.94 (d, 1H, J=8.8 Hz, 3"-H), 6.86 (d, 2H, Ph, AA'BB' system, J=8.7 Hz, 3'-H, 5'-H), 3.92 (s, 2H, CH$_2$), 3.75 (s, 3H, CH$_3$O). $^{13}$C NMR (100 MHz, DMSO-d$_6$): δ=173.8 (C=S), 162.4 (C=O), 160.1 (C4'), 152.7 (C2"), 150.0 (C6), 133.1 (C1'), 130.2 (C2'), 128.1 (C4"), 127.5 (C5"), 125.5 (C7"), 123.8 (C8"a), 122.8 (C6"), 121.9 (C8"), 118.5 (C3"), 116.6 (C1"), 115.0 (C5), 113.3 (C3'), 55.2 (CH$_3$O), 21.7 (CH$_2$). LR MS [ES$^+$]: m/z 412.99 [M+Na]$^+$ (100%); LR MS [ES$^-$]: m/z 388.73 [M−H]$^-$ (100%); HR MS [ES$^-$]: m/z calc'd for C$_{22}$H$_{17}$N$_2$O$_3$S 389.0960 [M−H]$^-$. found 389.0965 (+1.4 ppm).

Synthesis of 5-(2-Hydroxy-naphthalen-1-ylmethyl)-6-phenyl-1H-pyrimidine-2,4-dione (6a)

To a solution of NaOEt (2M) prepared dissolving Na metal into dry ethanol, urea (15.6 eq) and dihydrocoumarin 5a (1 eq) were added and the reaction refluxed for 18 h. After removing the solvent in vacuo, the crude reaction mixture was dissolved in distilled water and the products precipitated after addition of 2M aqueous HCl. The solid was collected by filtration and purified by recrystallization from ethanol. Yielded 40 mg (0.11 mmol, 20%) as a white powder after recrystallisation from CHCl$_3$. mp 292-295° C. IR (NaCl, thin layer) v$_{max}$: 3417 and 3105 (OH), 2923 (CH$_2$), 1653.7 (C=O), 1576.4 (NH), 1456 (C—N), 1119 (C—O, C=S). $^1$H NMR (400 MHz, DMSO-d$_6$): δ=11.33 (br, 1H, NH), 10.90 (br, 1H, NH), 9.64 (s, 1H, OH), 7.65 (d, 1H, $^3$J=7.8 Hz, $^4$J=1.8 Hz, 5"-H), 7.50 (d, 1H, J=8.8 Hz, 4"-H), 7.46-7.35 (m, 3H, 8-H, 2×Ph), 7.31 (ddd, 2H, $^3$J=8.3 Hz, $^4$J=1.5 Hz, 2×Ph), 7.19-7.08 (m, 3H, 7"-H, 6"-H+1×Ph), 6.92 (d, 1H, J=8.8 Hz, 3"-H), 3.90 (s, 2H, CH$_2$). $^{13}$C NMR (100 MHz, DMSO-d$_6$): δ=166.0 (C=O), 152.8 (C2"), 150.3 (C=O), 133.0 (C1'), 132.6 (C8"a), 129.4 (5"), 128.4 (2×Ph), 128.2 (C4"a), 128.1 (2×Ph), 127.5 (C4'), 125.4 (C7"), 122.8 (C8"), 121.9 (C6"), 118.8 (C3"), 117.3 (C1"), 109.3 (C5), 21.2 (CH$_2$). LR MS [ES$^+$]: m/z 367.04 [M+Na]$^+$ (100%); LR MS [ES$^-$]: m/z 342.81 [M−H]$^-$ (100%); HR ES [MS$^-$]: m/z calc'd for C21H16N2O3Na 367.1059 [M−H]$^-$. found 367.1056 (−0.7 ppm).

Scheme 2: Synthesis of analog 6d

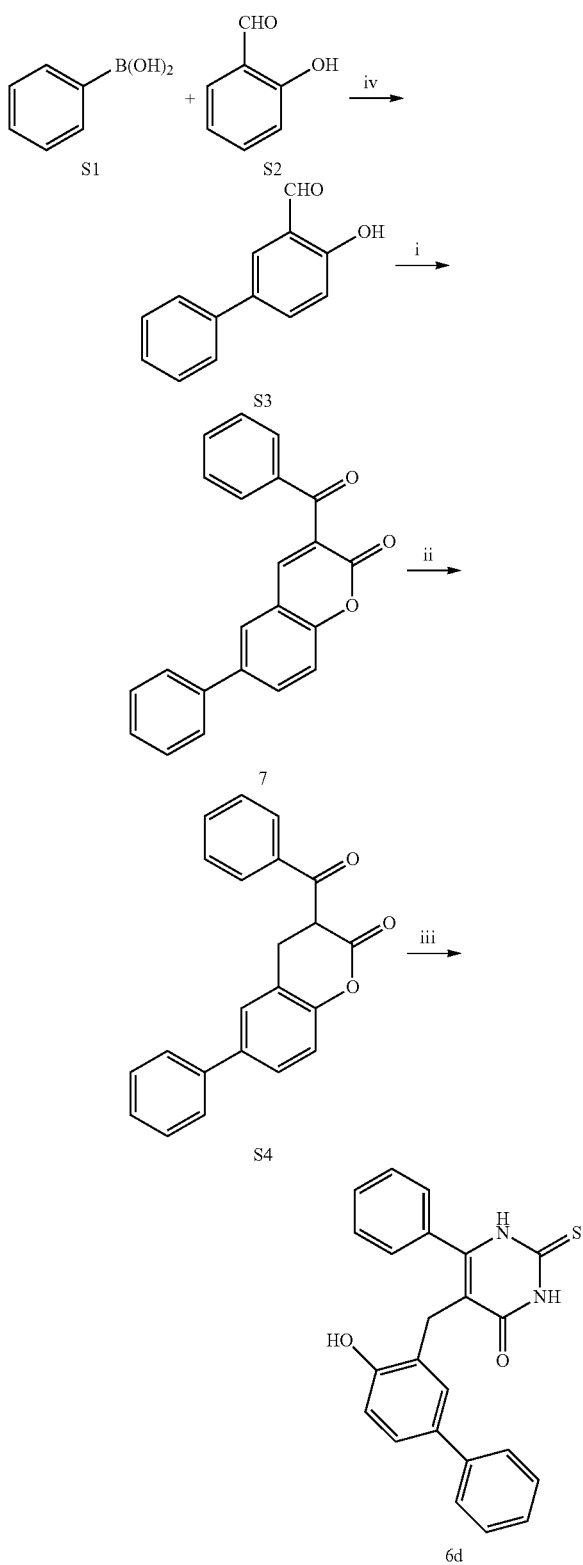

Reagents and conditions: (iv) Pd(dppf)Cl$_2$.CH$_2$Cl$_2$, K$_2$CO$_3$, DME:H$_2$O (3:1), reflux, 4 h, 50%. (i) Ethyl benzoylacetate (8a), piperidine, EtOH, reflux, 2 h, 66% (ii) NaBH$_4$, pyridine, rt, 2.5 h, 94%. (iii) Na, thiourea, EtOH, reflux, 18 h, 40%.

2-Hydroxy-5-phenylbenzaldehyde (S3)

(Fahmy, A. M.; Revue Roumaine de Chimie 1985, V30(8), P749-52) Bromosalicaldehyde (S1, 525 mg, 2.6 mmol), phenylboronic acid (S2, 349 mg, 2.86 mmol), Pd(dppf)Cl$_2$.CH$_2$Cl$_2$ (106 mg, 0.13 mmol) and Na$_2$CO$_3$ (413 mg, 3.9 mmol) were dissolved in degassed DME/H$_2$O (3:1) and stirred at reflux (100° C.) for 5 h. After cooling, the mixture was poured into water and extracted with DCM (3×100 ml). The combined organic layers were dried over Na$_2$SO$_4$ and the residue purified by silica gel chromatography (Et$_2$O, 100%) to afford the title compound (250 mg, 50%).

2-Hydroxy-5-phenylbenzaldehyde (S3)

Yielded 250 mg (1.26 mmol, 50%) as a white-red powder. $^1$H NMR (400 MHz, CDCl$_3$): δ=10.99 (s, 1H, OH), 9.97 (s, 1H, CHO), 7.79-7.74 (m, 2H, 1×Ph, 6-H), 7.56-7.52 (m, 2H, Ph), 7.44 (ddd, 2H, $^3$J=7.3 Hz, $^4$J=1.4 Hz, Ph), 7.35 (ddd, 1H, $^3$J=7.3 Hz, $^4$J=1.2 Hz, Ph), 7.15 (d, 1H, J=8.6 Hz, 3-H).

3-Benzoyl-6-phenyl-chromen-2-one (7)

Yielded 235 mg (0.72 mmol, 66%) as a white-yellow powder. m. p. 166-168° C. $^1$H NMR (400 MHz, CDCl$_3$): δ=8.14 (s, 1H, 1-H), 7.93-7.84 (m, 3H, Ph), 7.77 (s, 1H, J=2.1 Hz, 7-H), 7.66-7.56 (m, 3H, Ph), 7.54-7.45 (m, 5H, Ph), 7.41 (ddd, 1H, Ar, $^3$J=7.3 Hz, $^4$J=1.3 Hz, Ph).

2-Benzoyl-6a-phenyl-chroman-2-one (S4)

Yielded 200 mg (0.61 mmol, 94%) as a white-yellow powder. $^1$H NMR (400 MHz, CDCl$_3$): δ=8.00-7.94 (m, 2H, Ph), 7.63 (ddd, 1H, $^3$J=6.5 Hz, $^4$J=1.2 Hz, Ph), 7.56-7.47 (m, 5H, Ph), 7.47-7.38 (m, 3H, Ph), 7.34 (ddd, 1H, $^3$J=6.2 Hz, $^4$J=1.4 Hz, Ph), 7.18 (d, 1H, J=8.4 Hz, Ph), 4.75 (dd, 1H, J=6.4 Hz, 2-H), 3.60 (dd, 1H, J=9.6 Hz, 1-H), 3.25 (dd, 1H, J=6.4 Hz, 1-H).

5-(4-Hydroxy-biphenyl-3-ylmethyl)-6-phenyl-2-thioxo-2,3-dihydro-1H-pyrimidin-4-one (6d)

Yielded 80 mg (40%) as a white powder after recrystallisation from ethanol. mp 251-256° C. IR (NaCl, thin layer) v max: 3417 (OH), 1628 (CO), 1119 (C=S). $^1$H NMR (400 MHz, DMSO-d$_6$): 12.59 (br, 1H, NH), 12.46 (br, 1H, NH), 9.49 (s, 1H, OH), 7.49-7.34 (m, 9H), 7.31-7.22 (m, 2H), 6.99 (d, 1H, J=2.1 Hz), 6.80 (d, 1H, J=8.3 Hz, 3"-H), 3.41 (s, 2H, CH$_2$). $^{13}$C NMR (100 MHz, DMSO-d$_6$): 174.5 (C=S), 161.9 (C=O), 154.5 (C2"), 151.4 (C6), 140.4, 131.6, 130.8, 129.9, 128.8, 128.3, 128.2, 126.2, 126.0, 126.0, 125.2, 115.1, 113.0, 25.3 (CH$_2$). LR MS [ES$^-$]: m/z 385.06 [M–H]$^-$ (100%); HR MS [ES$^-$]: m/z calc'd for C$_{23}$H$_{17}$N$_2$O$_2$S 385.1011 [M–H]$^-$. found 385.1013 (+0.6 ppm).

Synthesis of N-1 Substituted Analogs of 1: Overview

Analog 6e was prepared by reaction of 5a with N-methylthiourea and sodium ethoxide. Structural assignment of 6e was achieved using 2D [$^1$H, $^{13}$C] HMBC analysis. The observed regiochemistry may be rationalised by initial reaction of the most nucleophilic nitrogen atom in N-methylthiourea with the most reactive carbonyl group, the aryl ketone, in 5a. The encouraging inhibition and selectivity data for SIRT2 shown by 6e (Table 4) led to the synthesis of further analogs in which different N1-aliphatic chains (R$^1$) were incorporated.

Synthesis of N-1 Substituted Analogs of 1: Specific Syntheses 5-(2-Hydroxy-naphthalen-1-ylmethyl)-1-methyl-6-phenyl-2-thioxo-2,3-dihydro-1H-pyrimidin-4-one (6e)

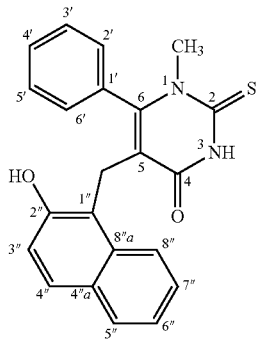

Yielded 40 mg (0.10 mmol, 16%) as a white powder after recrystalisation from CHCl$_3$. mp 254-257° C. IR (NaCl, thin layer) v$_{max}$: 3348 (OH), 2804 (CH$_2$), 1628 (C=O), 1556 (NH), 1431 (CSNH), 1212, (C=S), 877, 766 and 702 (C—H$_{Ar}$). $^1$H NMR (400 MHz, DMSO-d$_6$): δ=12.80 (br, 1H, NH), 9.22 (br, 1H, OH), 7.65 (d, 1H, J=7.8 Hz, 5"-H), 7.51-7.47 (m, 2H, 4"-H, 8"-H), 7.30-7.11 (m, 5H, 6"-H, 7"-H+3× Ph), 6.97 (d, 2H, J=7.0 Hz, Ph), 6.85 (d, 1H, J=8.8 Hz, 3-H), 3.82 (s, 2H, CH$_2$), 3.16 (s, 3H, CH$_3$). $^{13}$C NMR (100 MHz, DMSO-d$_6$): δ=175.2 (C=S), 160.6 (C=O), 152.7 (C2"), 152.0 (C6), 133.1, 132.2, 128.9, 128.3 (C3', C5'), 128.0, 127.9, 127.7 (C2', C6'), 127.2, 125.8, 125.5, 122.7, 122.1, 121.7, 118.5, 117.9 (C3"), 116.2, 40.2 (CH$_3$), 22.0 (CH$_2$). LR MS [ES$^+$]: m/z 397.08 [M+Na]$^+$ (100%); LR MS [ES$^-$]: m/z 373.05 [M−H]$^-$ (100%); HR MS [ES$^-$]: m/z calc'd for C$_{22}$H$_{17}$N$_2$O$_2$S 373.1011 [M−H]$^-$. found 373.1010 (−0.2 ppm).

1-Ethyl-5-(2"-hydroxy-naphthalen-1-ylmethyl)-6-phenyl-2-thioxo-2,3-dihydro-1H-pyrimidin-4-one (6f)

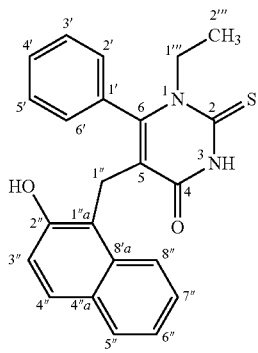

Yielded 30 mg (0.07 mmol, 20%) as a white powder after column chromatography in EtOAc-hexane (1:4) and re-crystallisation from ethanol. m. p. 256-258° C. v$_{max}$,cm$^{-1}$ 3111 (OH), 1628.3 (C=O), 1212.9 (C=S). IR (NaCl, thin layer) v$_{max}$/cm$^{-1}$ 3676, 2988 and 2972 (OH), 2902 (CH$_2$, CH$_3$), 1633 (C=O), 1437 (C—N), 1394 and 1241 (OH), 1217 and 1103 (C=S), 1076, 1057 and 1028 (C—O), 812, 767 and 741 (C—H$_{Ar}$). $^1$H NMR (DMSO-d$_6$, 400 MHz): δ=12.75 (br, 1H, NH), 9.20 (br, 1H, OH), 7.65 (d, 1H, J=7.1 Hz, H-5'), 7.51-7.45 (m, 2H, H-4", H-8"), 7.27-7.17 (m, 5H, H-6", H-7", H-3', H-4', H-5'), 6.98 (d, 2H, J=7.1 Hz, H-2', H-6'), 6.84 (d, 1H, J=8.6 Hz, H-3"), 3.86 (br, 2H, H-1'''), 3.77 (s, 2H, H-1"'), 0.92 (t, 3H, J=7.0 Hz, H-2'''). $^{13}$C NMR (DMSO-d$_6$, 100 MHz): 175.5 (C=S), 161.4 (C=O), 153.6 (C2"), 152.6 (C6), 132.7 (C8"a), 131.6 (C1'), 129.1 (C4'), 128.9 (C3', C5'), 128.9 (C4"a), 128.3 (C2', C6'), 127.9 (C5"), 127.2 (C4"), 126.5 (C7"), 123.6 (C8"), 122.8 (C6"), 118.9 (C3"), 117.2 (C1"a), 116.1 (C5), 46.9 (C1'''), 23.0 (C1"), 13.7 (C2'''). LR MS [ES$^+$]: m/z 411.33 [M+Na]$^+$ (100%). LR MS [ES$^-$]: m/z 387.16 [M−H]$^-$ (100%); HR MS [ES$^+$]: m/z calc'd for C$_{23}$H$_{20}$N$_2$O$_2$SNa 411.1143 [M+Na]$^+$. found 411.1149 (+1.3 ppm).

1-Allyl-5-(2"-hydroxy-naphthalen-1-ylmethyl)-6-phenyl-2-thioxo-2,3-dihydro-1H-pyrimidin-4-one (6g)

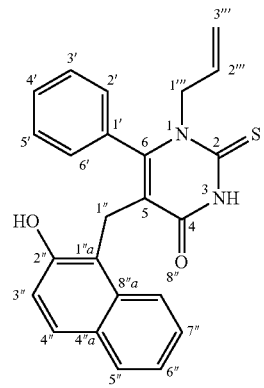

Yielded 20 mg (0.05 mmol, 15%) as a white powder after column chromatography in EtOAc-hexane (1:4) and re-crystallisation from ethanol. m. p. 175-177° C. IR (NaCl, thin layer) v$_{max}$/cm$^{-1}$ 3676 and 2988 (OH), 2902 (CH$_2$), 1626 (C=O), 1479 (CSNH), 1406, 1394 and 1242 (OH), 1075, 1057 and 1028 (C—O), 892, 823 and 747 (C—H$_{Ar}$), 701 (C—H). $^1$H NMR (DMSO-d$_6$, 300 MHz): δ=12.82 (br, 1H, NH), 9.22 (br, 1H, OH), 7.65 (d, 1H, J=7.1 Hz, H-5"), 7.52-7.43 (m, 2H, H-4", H-8"), 7.28-7.18 (m, 5H, H-6", H-7", H-3', H-4', H-5'), 6.93 (d, 2H, J=7.0, H-2', H-6'), 6.85 (d, 1H, J=8.8 Hz, H-3"), 5.61-5.50 (m, 1H, H-2'''), 4.98 (dd, 1H, $^3$J=10.5 Hz, $^4$J=1.2 Hz, H-3'''), 4.64 (dd, 1H, $^3$J=17.3 Hz, $^4$J=1.2 Hz, H-3'''), 4.50 (m, 2H, H-1'''), 3.78 (s, 2H, H-1"). $^{13}$C NMR (DMSO-d$_6$, 100 MHz): δ=174.8 (C=S), 160.7 (C=O), 152.7 (C2"), 151.7 (C6), 133.0 (C8"a), 131.9 (C2'''), 131.4 (C1'), 128.9 (C3', C5'), 128.4 (C2', C6'), 128.1 (C5"), 128.0 (C4'), 127.8 (C4"a), 127.2 (C4"), 125.5 (C7"), 122.5 (C8"), 121.7 (C6"), 117.8 (C3"), 117.1 (C3'''), 116.5 (C1'a), 116.1 (C5), 52.5 (C1'''), 22.19 (C1"). LR MS [ES$^+$]: m/z 423.12 [M+Na]$^+$ (100%). HR MS [ES$^+$]: m/z calc'd for C$_{24}$H$_{20}$N$_2$O$_2$NaS 423.1143 [M+Na]$^+$. found 423.1142 (−0.3 ppm).

5-(2''-Hydroxy-naphthalen-1-ylmethyl)-6-phenyl-1-propyl-2-thioxo-2,3-dihydro-1H-pyrimidin-4-one (6h)

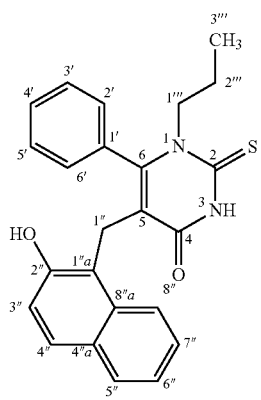

Yielded 16 mg (0.04 mmol, 10%) as a white powder after column chromatography (EtOAc-Hexane 1:4) and re-crystallisation from ethanol. m. p. 227-229° C. IR (NaCl, thin layer) $v_{max}$/cm$^{-1}$ 3676 and 2988 (OH), 2969 and 2902 (CH$_3$, CH$_2$), 1630 (C=O), 1482 (CSNH), 1432 (C—N), 1206, 1131 and 1108 (C=S), 1075, 1066 and 1057 (C—O), 880, 820 and 767 (C—H$_{Ar}$), 745, 701 and 666 (C—H). $^1$H NMR (DMSO-$_{d6}$, 400 MHz): δ=12.77 (br, 1H, NH), 9.21 (s, 1H, OH), 7.65 (d, 1H, J=8.8 Hz, H-5''), 7.55-7.45 (m, 2H, H-4'', H-8''), 7.29-7.12 (m, 5H, H-6'', H-7'', H-3', H-4', H-5'), 6.97 (d, 2H, J=7.0 Hz, H-2', H-6'), 6.84 (d, 1H, J=8.8 Hz, H-3''), 3.78 (s, 2H, H-1''), 3.69 (br, 2H, H-1'''), 1.41 (m, 2H, H-2'''), 0.43 (t, 3H, J=7.4 Hz, H-3'''). $^{13}$C NMR (DMSO-$_{d6}$, 100 MHz): δ=174.8 (C=S), 160.4 (C=O), 152.7 (C2''), 151.7 (C6), 133.1 (C8''a), 131.7 (C1'), 129.3 (C4'), 128.9 (C5', C3'), 128.6 (C2', C6'), 128.1 (C5''), 128.0 (C4''), 127.8 (C4''a), 125.6 (C7''), 122.6 (C8''), 121.8 (C6''), 119.0 (C1''a), 117.9 (C3''), 116.2 (C5), 52.1 (C1'''), 22.1 (C1''), 20.3 (C2'''), 10.5 (C3'''). HR MS [ES$^+$]: m/z calc'd for C$_{24}$H$_{22}$N$_2$O$_2$NaS 425.1300 [M+Na]$^+$. found 425.1307 (+0.2 ppm).

1-butyl-5-((2''-hydroxynaphthalen-1-yl)methyl)-6-phenyl-2-thioxo-2,3-dihydropyrimidin-4(1H)-one (6j)

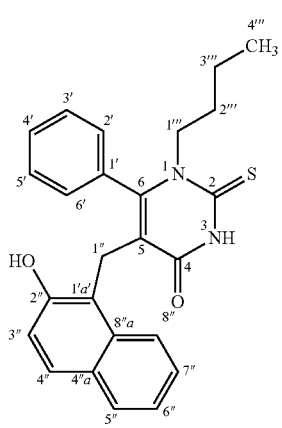 [SMILES: CCCCn1c(-c2ccccc2)c(Cc2c(O)ccc3ccccc23)c(=O)[nH]c1=S]

Yielded 29 mg (0.07 mmol, 7%) as a white powder after column chromatography (EtOAc-Hexane 1:9) and re-crystallisation from ethanol. m. p. 201-203° C. IR (NaCl, thin layer) $v_{max}$/cm$^{-1}$ 3667 and 3213 (OH), 2972 and 2902 (CH$_3$, CH$_2$), 1645 (C=O), 1487 (CSNH), 1428 (C—N), 1394 and 1233 (OH), 1204, 1179, 1129 and 1104 (C=S), 1067 and 1057 (C—O), 823 and 747, (C—HAr), 705 and 756 (C—H). $^1$H NMR (DMSO-$_{d6}$, 400 MHz): δ=12.75 (s, 1H, NH), 9.20 (s, 1H, OH), 7.65 (d, 1H, J=8.2 Hz, H-5''), 7.51-7.45 (m, 2H, H-8'', H-4''), 7.24-7.14 (m, 5H, H-7'', H-6'', H-3', H-4, H-5'), 6.98 (d, 2H, J=7.0 Hz, H-2', H-6'), 6.84 (d, 1H, J=8.7 Hz, H-3''), 3.79 (s overlapped with br, 4H, H-1'', H-1'''), 1.40 (br, 2H, H-2'''), 0.90-0.80 (m, 2H, H-3'''), 0.50 (t, 3H, J=7.3 Hz, H-4'''). $^{13}$C NMR (DMSO-$_{d6}$, 100 MHz): δ=174.6 (C=S), 160.4 (C=O), 152.7 (C2''), 151.7 (C6), 133.1 (C8''a), 131.6 (C1'), 128.9 (C3', C5'), 128.1 (C2', C6'), 128.0 (C4'), 128.0 (C5''), 127.9 (C4''a), 127.6 (C4''), 125.6 (C7''), 122.6 (C8''), 121.8 (C6''), 119.1 (C5), 117.9 (C1''a), 116.2 (C3''), 50.3 (C1'''), 28.6 (C2'''), 22.0 (C1''), 18.9 (C3'''), 12.9 (C4'''). LR MS [ES$^+$]: m/z 439.05 [M+Na]$^+$ (100%); LR MS [ES$^-$]: m/z 415.16 [M–H]$^-$ (100%); HR MS [ES$^+$]: m/z calc'd for C$_{25}$H$_{24}$N$_2$O$_2$SNa 439.1456 [M+Na]$^+$. found 439.1473 (+3.8 ppm).

Parallel Synthesis Approach: Summary

Encouraged by the yields and easy work-up associated with the synthesis of analogs of 1 and the initial observation that incorporation of substituents into the phenyl ring of 1 resulted in tuning of the required biological activity (Table 4 below), additional analogs were prepared using a parallel synthesis approach. The commercial availability of a range of ethyl benzoylacetates enabled the rapid incorporation of different electron-withdrawing or electron-donating substituents at the required positions. 19 ethyl benzoylacetates (R$_a$, 3i-xix) were loaded with 2 into different vessels of a Buchi greenhouse parallel synthesis apparatus. Ethanol and piperidine were then added and in 18 of the 19 cases the desired product (4i-xviii) formed on heating in high yields (45-98%) as yellow precipitates. Subsequent reduction of 4i-xviii afforded 15 1,2-dihydroketocoumarins 5i-xv following precipitation of the product on addition of aqueous hydrochloric acid (2M) to the crude reaction mixture. Analytically pure samples of 5i-xv were obtained by recrystallization from ethanol in a wide range of yields (35-95%). Interestingly, $^1$H NMR analysis of ortho-substituted analog 5vii showed that it existed predominantly as the enol-lactone isomer (see tautomeric structure below). A modified protocol compared with that employed to prepare 1 was used for substrates 5i-xv. Addition of the sodium ethoxide solution as the final step and heating at reflux for 24 hours was followed by removal of the solvent in parallel and dissolution of the resulting solids in water. Subsequent acidification of the aqueous solutions afforded 11 new cambinol analogs 6i-xi in moderate yields after purification by column chromatography.

General Protocol for the Synthesis of 3-benzoylbenzo[f]coumarins 4i-4xviii

Different phenyl substituted ethyl benzoylacetate 3 (1eq) and 2-hydroxy-1-naphthaldehyde 2 (1 eq) were mixed together into different vessels of the parallel synthesis apparatus and ethanol (4 mL) was added. The reaction was warmed to 50° C. and piperidine (5 drops) was added. The reaction was refluxed for 2 h and the solid products were collected by parallel filtration and washed with ethanol.

TABLE 1

Yields observed for the products of the first step of the parallel synthesis.

| Compound | $R_1$ | Yield (%) |
|---|---|---|
| 4b | p-Br—Ph | 93 |
| 4i | o-CH$_3$—Ph | 79 |
| 4ii | m-CH$_3$—Ph | 66 |
| 4iii | p-CH$_3$—Ph | 62 |
| 4iv | p-Cl—Ph | 74 |
| 4v | p-I—Ph | 98 |
| 4vi | p-CF$_3$—Ph | 77 |
| 4vii | o-Br—Ph | 76 |
| 4viii | m-Br—Ph | 83 |
| 4ix | m-Cl—Ph | 87 |
| 4x | o-F—Ph | 86 |
| 4xi | m-F—Ph | 79 |

2-(5'-Bromo-benzoyl)-benzo[f]chromen-3-one (4b)

Yielded 600 mg (1.58 mmol, 93%) as a yellow powder. Analytical characterisation was identical to that of 4b prepared as described above.

2-(3'-Methyl-benzoyl)-benzo[f]chromen-3-one (4i)

Yielded 624 mg (1.98 mmol, 79%) as a yellow powder. m. p. 208-210° C. $^1$H NMR (CDCl$_3$, 300 MHz): δ=9.02 (s, 1H, H-1), 8.27 (d, 1H, J=8.2 Hz, H-10), 8.12 (d, 1H, J=9.0 Hz, H-6), 7.95 (d, 1H, J=7.6 Hz, H-7), 7.77-7.71 (m, 1H, H-9), 7.66-7.60 (m, 1H, H-8), 7.54-7.46 (m, 2H, H-5, ArH), 7.47-7.40 (m, 1H, ArH), 7.36-7.31 (m, 1H, ArH), 7.26 (m, 1H, overlapped with solvent signal, ArH), 2.55 (s, 3H, CH$_3$). LR MS [ES$^+$]: m/z 337.11 [M+Na]$^+$ (100%).

2-(4'-Methyl-benzoyl)-benzo[f]chromen-3-one (4ii)

Yielded 280 mg (0.89 mmol, 36%) as a yellow powder. m. p. 194-196° C. $^1$H NMR (CDCl$_3$, 300 MHz): δ=8.91 (s, 1H, H-1), 8.27 (d, 1H, J=8.4 Hz, H-10), 8.11 (d, 1H, J=9.1 Hz, H-6), 7.96 (d, 1H, J=7.6 Hz, H-7), 7.78-7.66 (m, 3H, H-9+2× ArH), 7.66-7.62 (m, 1H, H-8), 7.53 (d, 1H, J=9.1 Hz, H-5), 7.47-7.34 (m, 2H, ArH), 2.42 (s, 3H, CH$_3$). LR MS [ES$^+$]: m/z 337.11 [M+Na]$^+$ (100%).

2-(5'-Methyl-benzoyl)-benzo[f]chromen-3-one (4iii)

Yielded 490 mg (1.56 mmol, 62%) as a yellow powder. m. p. 190-192° C. IR (NaCl, thin layer) v$_{max}$/cm$^{-1}$ 1745 (CO), 1224, 1147, 1139 (C—O), 1678 (C—Cl). $^1$H NMR (CDCl$_3$, 300 MHz): δ=8.89 (s, 1H, H-1), 8.26 (d, 1H, J=8.2 Hz, H-10), 8.10 (d, 1H, J=9.0 Hz, H-6), 7.95 (d, 1H, J=8.1 Hz, H-7), 7.83 (d, 2H, AA'BB' system, J=8.0 Hz, H-3', H-7'), 7.76-7.71 (m, 1H, H-9), 7.66-7.60 (m, 1H, H-8), 7.52 (d, 1H, J=9.0 Hz, H-5), 7.30 (d, 2H, AA'BB' system, J=8.0 Hz, H-4', H-6'), 2.44 (s, 3H, CH$_3$). $^{13}$C NMR (CDCl$_3$, 100MHz): δ=191.7 (C1'), 158.7 (C3), 155.3 (C4a), 144.8 (C5'), 141.5 (C1), 135.3 (C6), 133.8 (C2'), 130.3 (C6a), 129.9 (C3', C7'), 129.4 (C2', C6'), 129.3 (C10a), 129.1 (C7), 128.7 (C9), 126.6 (C2), 126.4 (C8), 121.5 (C10), 116.6 (C5), 112.9 (C10b). HR MS [ES$^+$]: m/z calc'd for C$_{21}$H$_{14}$ONa 337.0935 [M+Na]$^+$. found 337.0928 (−2.0 ppm).

2-(5'-Chloro-benzoyl)-benzo[f]chromen-3-one (4iv)

Yielded 614 mg (1.83 mmol, 74%) as a yellow powder. m. p. 230-233° C. (litt. 232-233° C.). $^1$H NMR (CDCl$_3$, 400 MHz): δ=8.97 (s, 1H, H-1), 8.28 (d, 1H, J=8.3 Hz, H-10), 8.12 (d, 1H, J=9.0 Hz, H-6), 7.96 (d, 1H, J=7.8 Hz, H-7), 7.86 (d, 2H, AA'BB' system, J=8.9 Hz, H-3', H-7'), 7.78-7.70 (m, 1H, H-9), 7.66-7.60 (m, 1H, H-8), 7.52 (d, 1H, J=9.0 Hz, H-5), 7.47 (d, 2H, AA'BB' system, J=8.9 Hz, H-4', H-6'). LR MS [ES$^+$]: m/z 357.03 [M+Na]$^+$ (100%).

2-(5'-Iodo-benzoyl)-benzo[f]chromen-3-one (4v)

Yielded 874 mg (2.05 mmol, 82%) as a yellow powder. m. p. 249-252° C. $^1$H NMR (CDCl$_3$, 400 MHz): δ=8.97 (s, 1H, H-1), 8.28 (d, 1H, J=8.3 Hz, H-10), 8.13 (d, 1H, J=9.0 Hz, H-6), 7.96 (d, 1H, J=8.0 Hz, H-7), 7.86 (d, 2H, AA'BB' system, J=8.5 Hz, H-3', H-7'), 7.78-7.70 (m, 1H, H-9), 7.67-7.61 (m, 3H, H-8+2×ArH, AA'BB' system, J=8.5 Hz, H-4', H-6'), 7.52 (d, 1H, J=9.0 Hz, H-5). LR MS [ES+]: m/z 449.04 [M+Na]$^+$ (100%).

2-(5'-Trifluoromethyl-benzoyl)-benzo[f]chromen-3-one (4vi)

Yielded 707 mg (1.92 mmol, 77%) as a yellow powder. m. p. 192-195° C. $^1$H NMR (CDCl$_3$, 400 MHz): δ=9.00 (s, 1H, H-1), 8.30 (d, 1H, J=8.3 Hz, H-10), 8.14 (d, 1H, J=9.0 Hz, H-6), 7.99 (d, 2H, AA'BB' system, J=8.0 Hz, H-3', H-7'), 7.96 (d, 1H, J=8.7 Hz, H-7), 7.79-7.72 (m, 3H, H-9, 2×ArH, AA'BB∝ system, J=8.0 Hz, H-4', H-6'), 7.68-7.64 (m, 1H, H-8), 7.53 (d, 1H, J=9.0 Hz, H-5). LR MS [ES$^+$]: m/z 391.09 [M+Na]$^+$ (100%).

2-(3'-Bromo-benzoyl)-benzo[f]chromen-3-one (4vii)

Yielded 761 mg (2.01 mmol, 76%) as a yellow powder. m. p. 238-240° C. $^1$H NMR (CDCl$_3$, 400 MHz): δ=9.27 (s, 1H, H-1), 8.36 (d, 1H, J=8.3 Hz, H-10), 8.13 (d, 1H, J=8.8 Hz, H-6), 7.95 (d, 1H, J=7.8 Hz, H-7), 7.80-7.71 (m, 1H, H-9), 7.63 (m, 2H, H-8, ArH), 7.55-7.43 (m, 3H, H-5+2×ArH), 7.41-7.36 (m, 1H, ArH). LR MS [ES$^+$]: m/z 401.05 [M+Na]$^+$ (100%).

2-(4'-Bromo-benzoyl)-benzo[f]chromen-3-one (4viii)

Yielded 785 mg (2.07 mmol, 83%) as a yellow powder. m. p. 213-215° C. IR (NaCl, thin layer) v$_{max}$/cm$^{-1}$ 1708 (CO), 1275, 1210 (C—O), 750, 666 (C—Br). $^1$H NMR (CDCl$_3$, 400 MHz): 8.98 (s, 1H, H-1), 8.29 (d, 1H, J=8.3 Hz, H-10), 8.13 (d, 1H, J=9.0 Hz, H-6), 8.04 (t, 1H, J=1.8 Hz, H-3'), 7.96 (d, 1H, J=8.1 Hz, H-7), 7.84-7.79 (m, 1H, ArH), 7.78-7.72 (m, 2H, H-9, ArH), 7.66-7.50 (m, 1H, H-8), 7.53 (d, 1H, J=9.0 Hz, H-5), 7.37 (t, 1H, J=7.8 Hz, ArH). $^{13}$C NMR (CDCl$_3$, 100MHz): δ=192.3 (C1'), 158.3 (C3), 156.5 (C4a), 143.7 (C1), 140.8 (C4'), 136.5 (C6), 133.1 (Ar), 132.1 (Ar), 130.4 (C6a), 129.7 (Ar), 129.4 (C9), 129.3 (C7), 129.2 (C10a), 127.8 (Ar), 126.8 (C8), 123.7 (C2), 122.8 (C10), 119.6 (C2'), 116.9 (C5), 113.2 (C10b). HR MS [ES$^+$]: m/z calc'd for C$_{20}$H$_{11}$O$_3$Na$^{79}$Br 400.9789 [M+Na]$^+$. found 400.9786 (−0.8 ppm); m/z calc'd for C$_{20}$H$_{11}$O$_3$Na$^{81}$Br 402.9769 [M+Na]$^+$. found 402.9785 (−1.9 ppm).

2-(4'-Chloro-benzoyl)-benzo[f]chromen-3-one (4ix)

Yielded 722 mg (2.16 mmol, 87%) as a yellow powder. m. p. 228-230° C. $^1$H NMR (CDCl$_3$, 400 MHz): δ=8.98 (s, 1H, H-1), 8.29 (d, 1H, J=8.3 Hz, H-10), 8.14 (d, 1H, J=9.0 Hz, H-6), 7.96 (d, 1H, J=7.9 Hz, H-7), 7.90-7.86 (m, 1H, ArH), 7.78-7.72 (m, 2H, H-9, ArH), 7.67-7.60 (m, 1H, H-8), 7.62-7.58 (m, 1H, ArH), 7.53 (d, 1H, J=9.0 Hz, H-5), 7.46-7.42 (m, 1H, ArH). HR MS [Cl⁺]: m/z calc'd for $C_{20}H_{12}O_3Cl$ 335.0475 [M+H]⁺. found 335.0467 (−2.4 ppm).

2-(3'-Fluoro-benzoyl)-benzo[f]chromen-3-one (4x)

Yielded 685 mg (2.15 mmol, 86%) as a yellow powder. m. p. 190-192° C. ¹H NMR (CDCl₃, 300 MHz): δ=9.08 (s, 1H, H-1), 8.35 (d, 1H, J=8.4 Hz, H-10), 8.11 (d, 1H, J=8.9 Hz, H-6), 7.89-7.75 (m, 2H, H-9, H-6), 7.67-7.61 (m, 1H, H-8), 7.59-7.54 (m, 2H, ArH), 7.51 (d, 1H, J=8.9 Hz, H-5), 7.34-7.30 (m, 1H, ArH), 7.13-7.09 (m, 1H, ArH). LR MS [ES⁺]: m/z 341.05 [M+Na]⁺ (100%).

2-(4'-Fluoro-benzoyl)-benzo[f]chromen-3-one (4xi)

Yielded 630 mg (1.98 mmol, 79%) as a yellow powder. m. p. 226-228° C. ¹H NMR (CDCl₃, 300 MHz): δ=8.98 (s, 1H, H-1), 8.29 (d, 1H, J=8.3 Hz, H-10), 8.14 (d, 1H, J=9.0 Hz, H-6), 7.99-7.92 (m, 1H, H-7), 7.77-7.71 (m, 1H, H-9), 7.70-7.62 (m, 1H, H-8), 7.66-7.59 (m, 2H, ArH), 7.53 (d, 1H, J=9.0 Hz, H-5), 7.47-7.41 (m, 1H, ArH), 7.38-7.30 (m, 1H, ArH). LR MS [ES⁺]: m/z 341.07 [M+Na]⁺ (100%).

General Protocol for the Parallel Synthesis of 5i-xv

NaBH₄ (1 eq) was added to the different solutions of 3-benzoyl-5,6-benzocoumarins 4 (1 eq) in dry pyridine (4 mL). The reactions were stirred at room temperature for 2 h. All the reactions were poured into cold aqueous HCl (2M) and white precipitates formed. The solids were collected by parallel filtration, washed with aqueous HCl (2M) and recrystallized in parallel from ethanol.

TABLE 2

Yields observed for the products of the second step of the parallel synthesis.

| Compound | R₁ | Yield (%) |
|---|---|---|
| 5b | p-Br—Ph | 93 |
| 5i | o-CH₃—Ph | 78 |
| 5ii | m-CH₃—Ph | 35 |
| 5iii | p-CH₃—Ph | 60 |
| 5iv | p-Cl—Ph | 90 |
| 5v | p-I—Ph | 85 |
| 5vi | p-CF₃—Ph | 89 |
| 5vii | o-Br—Ph | 80** |
| 5viii | m-Br—Ph | 90 |
| 5ix | m-Cl—Ph | 85 |
| 5x | o-F—Ph | 40 |
| 5xi | m-F—Ph | 62 |

*: product not recovered when the reaction was run in parallel;
**: yields refer to the reaction ran in normal glassware.

2-(5'-Bromobenzoyl)-1,2-dihydro-benzo[f]chromen-3-one (5b)

Yielded 280 mg (0.73 mmol, 93%) as a white powder. m. p. 221-223° C. ¹H NMR (CDCl₃, 400 MHz): δ=7.91-7.84 (m, 4H, H-7, H-10+2×ArH, AA'BB' system, J=8.6 Hz, H-4', H-6'), 7.82 (d, 1H, J=8.8 Hz, H-6), 7.65 (d, 2H, AA'BB' system, J=8.6 Hz, H-3', H-7'), 7.62-7.54 (m, 1H, H-9), 7.52-7.45 (m, 1H, H-8), 7.28 (d, 1H, J=8.8 Hz, H-5), 4.74 (dd, 1H, ³J=10.5 Hz, ³J=6.7 Hz, H-2), 3.83 (dd, 1H, ²J=16.6 Hz, ³J=10.5 Hz, H-1), 3.62 (dd, 1H, ³J=16.6 Hz, ²J=6.7 Hz, H-1). LR MS [Cl⁺]: m/z 337.06 [M+H]⁺ (100%).

2-(3'-Methyl-benzoyl)-1,2-dihydro-benzo[f]chromen-3-one (5i)

Yielded 310 mg (0.98 mmol, 78%) as a white powder. m. p. 123-126° C. ¹H NMR (CDCl₃, 300 MHz): δ=7.92-7.76 (m, 3H, H-7, H-10, ArH), 7.63 (d, 1H, J=7.8 Hz, H-6), 7.59-7.37 (m, 3H, H-9, H8, ArH), 7.34-7.19 (m, 3H, H-5+2×ArH), 4.69 (dd, 1H, ³J=8.7 Hz, ³'J=6.6 Hz, H-2), 3.79 (dd, 1H, ²J=16.5 Hz, ³J=8.8 Hz, H-1), 3.56 (dd, 1H, ²J=16.5 Hz, ³J=6.6 Hz, H-1), 2.24 (s, 3H, CH₃). LR MS [ES⁺]: m/z 337.11 [M+Na]⁺ (100%).

2-(4'-Methyl-benzoyl)-1,2-dihydro-benzo[f]chromen-3-one (5ii)

Yielded 65 mg (0.20 mmol, 35%) as a white powder. m. p. 180-183° C. ¹H NMR (CDCl₃, 300 MHz): δ=7.91-7.76 (m, 5H, H-10, H-7, H-6+2×ArH), 7.60-7.52 (m, 1H, H-9), 7.52-7.46 (m, 1H, H-8), 7.45-7.36 (m, 2H, ArH), 7.29 (d, 1H, J=9.0 Hz, H-5), 4.81 (dd, 1H, ³J=10.3 Hz, ³'J=6.9 Hz, H-2), 3.83 (dd, 1H, ²J=16.7 Hz, ³J=10.4 Hz, H-1), 3.61 (dd, 1H, ²J=16.7 Hz, ³J=6.9 Hz, H-1), 2.42 (s, 3H, CH₃). LR MS[ES⁺]: m/z 337.11 [M+Na]⁺ (100%).

2-(5'Methyl-benzoyl)-1,2-dihydro-benzo[f]chromen-3-one (5iii)

Yielded 230 mg (0.72 mmol, 60%) as a white powder. m. p. 173-175° C. ¹H NMR (CDCl₃, 300 MHz): δ=7.93-7.78 (m, 5H, H-10, H-7, H-6+2×ArH, H-7', H-3'), 7.60-7.52 (m, 1H, H-9), 7.51-7.44 (m, 1H, H-8), 7.34-7.24 (m, 3H, overlapped with solvent signal, H-5+2×ArH, H-4', H-6'), 4.80 (dd, 1H, ³J=10.1 Hz, ³'J=6.9 Hz, H-2), 3.84 (dd, 1H, ²J=16.6 Hz, ³J=10.2 Hz, H-1), 3.60 (dd, 1H, ²J=16.6 Hz, ³J=6.9 Hz, H-1), 2.43 (s, 3H, CH₃). LR MS [ES⁺]: m/z 337.14 [M+Na]⁺ (100%).

2-(5'Chlorobenzoyl)-1,2-dihydro-benzochromen-3-one (5iv)

Yielded 360 mg (1.07 mmol, 90%) as a white powder. m. p. 206-208° C. IR (NaCl, thin layer) $v_{max}$/cm⁻¹ 1755 (CO), 1223, 1148 (C—O), 1678 (C—Cl). ¹H NMR (CDCl₃, 400 MHz): δ=7.95 (d, 2H, AA'BB' system, J=8.8 Hz, H-3', H-7'), 7.85-7.91 (m, 2H, H-7, H-10), 7.82 (d, 1H, J=8.8 Hz, H-6), 7.61-7.53 (m, 1H, H-9), 7.42-7.54 (m, 3H, H-8+2×ArH, AA'BB' system, J=8.8 Hz, H-4', H-6'), 7.28 (d, 1H, J=8.8 Hz, H-5), 4.75 (dd, 1H, ³J=10.5 Hz, ³'J=6.8 Hz, H-2), 3.83 (dd, 1H, ²J=16.6 Hz, ³J=10.5 Hz, H-1), 3.61 (dd, 1H, ²J=16.6 Hz, ³J=6.8 Hz, H-1). ¹³C NMR (CDCl₃, 75.5 MHz): δ=192.9 (C1'), 165.9 (C3), 148.0 (C4a), 139.6 (C5'), 134.4 (C2'), 131.9 (C6A), 131.3 (C10a), 130.6 (C-3', C-7'), 129.6 (C6), 129.6 (C-4', C-6'), 129.5 (C7), 127.7 (C8), 125.7 (C9), 123.1 (C10), 117.3 (C5), 114.8 (C10b), 46.8 (C2), 23.3 (C1). HR MS [Cl⁺]: m/z calc'd for $C_{20}H_{14}O_3Cl$ 337.0631 [M+H]⁺. found 337.0630 (−0.4 ppm).

2-(5'-Iodobenzoyl)-1,2-dihydro-benzo[f]chromen-3-one (5v)

Yielded 340 mg (0.79 mmol, 85%) as a white powder. m. p. 229-233° C. ¹H NMR (CDCl₃, 300 MHz): δ=7.92-7.85 (m, 4H, H-7, H-10, 2×ArH, AA'BB' system, J=8.7 Hz, H-3', H-7'), 7.81 (d, 1H, J=8.8 Hz, H-6), 7.70 (d, 2H, AA'BB' system, J=8.7 Hz, H-4', H-6'), 7.61-7.53 (m, 1H, H-9), 7.53-7.45 (m, 1H, H-8), 7.28 (d, 1H, J=8.8 Hz, H-5), 4.73 (dd, 1H, ³J=10.5 Hz, ³'J=6.8 Hz, H-2), 3.82 (dd, 1H, ²J=16.6 Hz, ³J=10.6 Hz, H-1), 3.61 (dd, 1H, ²J=16.6 Hz, ³J=6.8 Hz, H-1). LR MS [Cl⁺]: m/z 428.99 [M+H]⁺ (30%).

2-(5'-Trifluoromethylbenzoyl)-1,2-dihydro-benzo[f]chromen-3-one (5vi)

Yielded 360 mg (0.97 mmol, 89%) as a white powder. m. p. 192-193° C. IR (NaCl, thin layer) $v_{max}$/cm⁻¹ 1710 (CO), 1251

(C—O), 747, 691 (C—F). $^1$H NMR (CDCl$_3$, 400 MHz): δ=8.12 (d, 2H, AA'BB' system, J=8.2 Hz, H-3', H-7'), 7.93-7.86 (m, 2H, H-7, H-10), 7.83 (d, 1H, J=8.8 Hz, 6-H), 7.78 (d, 1H, AA'BB' system, J=8.2 Hz, H-4', H-6'), 7.62-7.54 (m, 1H, H-9), 7.54-7.45 (m, 1H, H-8), 7.28 (d, 1H, J=8.8 Hz, H-5), 4.79 (dd, 1H, $^3$J=10.7 Hz, $^3$J=6.7 Hz, H-2), 3.85 (dd, 1H, $^2$J=16.6 Hz, $^3$J=10.8 Hz, H-1), 3.64 (dd, 1H, $^2$J=16.6 Hz, $^3$J=6.7 Hz, H-1). $^{13}$C NMR (CDCl$_3$, 75.5 MHz): δ=193.0 (C1'), 164.4 (C3), 147.9 (C4a), 137.4 (C2'), 134.9 (C5'), 131.7 (C10a), 131.1 (C6a), 129.5 (C3', C7'), 129.1 (C7), 128.7 (C6), 127.6 (C8), 126.1 (C4', C6'), 125.6 (C9), 122.9 (C10), 121.9 (CF$_3$), 117.0 (C5), 114.5 (C10b), 45.7 (C2), 21.8 (C1). HR MS [ES$^-$]: m/z calc'd for C$_{21}$H$_{12}$O$_3$F$_3$ 369.0739 [M–H]–. found 369.0737 (–0.5 ppm).

2-(3'-bromobenzoyl)-1H-benzo[f]chromen-3(2H)-one (5vii)

yielded 41 mg, (0.1 mmol, 80%) as a yellow powder.

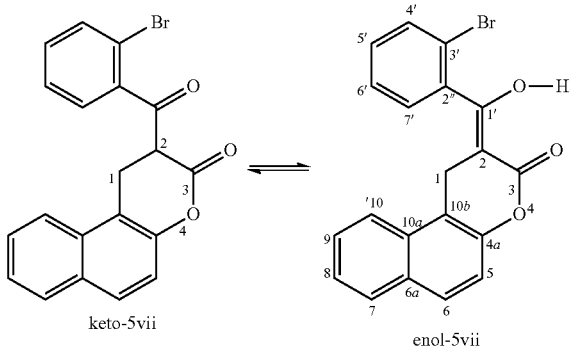 [SMILES: O=C1Oc2ccc3ccccc3c2CC1C(=O)c1ccccc1Br ; O=C1Oc2ccc3ccccc3c2C/C1=C(/O)c1ccccc1Br]

keto-5vii ⇌ enol-5vii

The $^1$H NMR spectrum of 5vii showed that keto-5vii exists as an equilibrium with enol-5vii (ratio of keto-5vii:enol-5vii=1:14). The signal derived from the proton at the C2 of keto-5vii was observed at δ=4.77 (dd, $^3$J=10.2 Hz, $^3$J=7.0 Hz). $^1$H NMR (enol-5vii) (CDCl3, 400MHz): δ=7.88-7.71 (m, 3H, H-10, H-7, H-6), 7.54-7.36 (m, 6H, H-9, H-8,+4× ArH), 7.28-7.21 (m, overlapping with solvent signal, 1H, H-5), 3.71 (br, 2H, H-1). $^{13}$C NMR (enol-5vii) (CDCl3, 75.5 MHz): δ=169.2 (C3), 164.2 (C1'), 147.5 (C4a), 135.3 (C2'), 133.6 (C4'), 131.6 (C6a), 131.0 (C10a), 129.2 (Ar), 129.1 (Ar), 128.8 (C7), 128.2 (Ar), 127.2 (C8), 125.4 (C9), 122.6 (C10), 120.9 (C3'), 117.4 (C5), 112.8 (C10b), 93.4 (C2), 23.7 (C1). HR MS [Cl$^+$]: m/z calc'd for C$_{20}$H$_{11}$O$_3$Na$^{79}$Br [M+Na]$^+$ 402.9769, found 402.9762 (–1.9 ppm).

2-(4'-Bromobenzoyl)-1,2-dihydro-benzo[f]chromen-3-one (5viii)

Yielded 340 mg (0.89 mmol, 90%) as a white powder. m. p. 219-221. IR (NaCl, thin layer) $v_{max}$/cm$^{-1}$ 1745 (CO), 1283, 1222, 1150 and 1071 (C—O), 743 (C—Br). $^1$H NMR (CDCl$_3$, 300 MHz): δ=7.97 (t, 1H, J=1.9 Hz, H-3'), 7.91-7.71 (m, 5H, H-10, H-7, H-6+2×ArH), 7.63-7.54 (m, 1H, H-9), 7.53-7.43 (m, 1H, H-8), 7.38 (t, 1H, J=7.9 Hz, ArH), 7.29 (d, 1H, J=8.9 Hz, H-5), 4.74 (dd, 1H, $^3$J=10.7 Hz, $^3$J=6.8 Hz, 2-H), 3.83 (dd, 1H, $^2$J=16.6 Hz, $^3$J=10.8 Hz, H-1), 3.62 (dd, 1H, $^2$J=16.6 Hz, $^3$J=6.8 Hz, H-1). $^{13}$C NMR (CDCl$_3$, 75.5 MHz): δ=192.8 (C1'), 164.5 (C3), 149.0 (C4a), 137.6 (C2'), 136.9 (C6'), 131.9 (Ar), 131.3 (C6a) 131.1 (C10a), 130.6 (Ar), 129.5 (C6), 129.0 (C7), 127.5 (C8), 127.4 (Ar), 125.6 (C9), 123.4 (C4'), 122.9 (C10), 117.0 (C5), 114.5 (C10b), 46.6 (C1), 23.1 (C2). LR MS [ES$^-$]: m/z 379.09 [M–H]$^-$ (100%).

2-(4'-Chloro-benzoyl)-1,2-dihydro-benzo[f]chromen-3-one (5ix)

Yielded 340 mg (1.01 mmol, 85%) as a white powder. m. p. 172-174° C. $^1$H NMR (CDCl$_3$, 300 MHz): δ=7.97 (t, 1H, J=1.8 Hz, H-3'), 7.92-7.85 (m, 3H, H-10, H-7, ArH), 7.82 (d, 1H, J=9.0 Hz, H-6), 7.63-7.54 (m, 2H, H-9, ArH), 7.52-7.42 (m, 2H, H-8, ArH), 7.29 (d, 1H, J=9.0 Hz, H-5), 4.74 (dd, 1H, $^3$J=10.7 Hz, $^3$J=6.8 Hz, H-2), 3.83 (dd, 1H, $^2$J=16.6 Hz, $^3$J=10.8 Hz, H-1), 3.62 (dd, 1H, $^2$J=16.6 Hz, $^3$J=6.8 Hz, H-1). LR MS [Cl$^+$]: m/z 337.06 [M+H]$^+$ (100%).

2-(3'-Fluoro-benzoyl)-1,2-dihydro-benzo[f]chromen-3-one (5x)

Yielded 50 mg (0.15 mmol, 40%) as a white powder. m. p. 122-124° C. $^1$H NMR (300 MHz, CDCl$_3$): δ=8.02-7.81 (m, 4H, H-10, H-7, H-6, ArH), 7.65-7.44 (m, 3H, H-9, H-8, ArH), 7.29 (d, 2H, J=8.6 Hz, H-5, ArH), 7.22-7.15 (m, 1H, ArH), 4.74 (dd, 1H, $^3$J=10.5 Hz, $^3$J=7.4 Hz, H-2), 3.76-3.64 (m, 2H, H-1). LR MS [ES$^+$]: m/z 343.09 [M+Na]$^+$ (100%).

2-(4'-Fluoro-benzoyl)-1,2-dihydro-benzo[f]chromen-3-one (5xi)

Yielded 77 mg (0.24 mmol, 62%) as a white powder. m. p. 143-145° C. $^1$H NMR (300 MHz, CDCl$_3$): δ=7.92-7.76 (m, 4H, H-10, H-7, H-6, ArH), 7.72-7.66 (m, 1H, ArH), 7.61-7.55 (m, 1H, H-9), 7.53-7.46 (m, 2H, H-8, ArH), 7.37-7.23 (m, 2H, H-5, ArH), 4.75 (dd, 1H, $^3$J=10.5 Hz, $^3$J=6.7 Hz, H-2), 3.84 (dd, 1H, $^2$J=16.6 Hz, $^3$J=10.5 Hz, H-1), 3.62 (dd, 1H, $^2$J=16.6 Hz, $^3$J=6.7 Hz, H-1). LR MS [ES$^+$]: m/z 343.11 [M+Na]$^+$ (100%); LR MS [ES$^-$]: m/z 319.10 [M–H]$^-$; HR MS [ES$^+$]: m/z calc'd for C$_{20}$H$_{13}$O$_3$NaF 343.0746 [M+Na]$^+$. found 343.0750 (+1.0 ppm).

General Procedure for the Parallel Synthesis of Cambinol Analogs 6i-6xi

Thiourea (15.6 eq) and different 2-benzoyl-5,6-benzo-1,2-dihydrocoumarins 5 (1 eq) were mixed into different vessels of the parallel synthesis apparatus and 5 ml of a 2M NaOEt stock solution, previously prepared dissolving Na metal into dry ethanol, was added to each reaction vessel and the reaction refluxed for 18 h. After removing the solvent in vacuo, the crude reaction mixtures were dissolved in distilled water and the products precipitated after addition of 2M aqueous HCl. The solids were collected by filtration and purified by column chromatography (EtOAc-hexane) and recrystallized from CHCl$_3$.

TABLE 3

Yields observed in the last step of the parallel synthesis.

| Compound | R$_1$ | Yield (%) |
|---|---|---|
| 6b | p-Br | 30 |
| 6i | o-CH$_3$ | 57 |
| 6ii | m-CH$_3$ | 51 |
| 6iii | p-CH$_3$ | 50 |
| 6iv | p-Cl | 18 |
| 6v | p-I | 22 |
| 6vi | p-CF$_3$ | 25 |
| 6vii | o-Br | 20 |
| 6viii | m-Br | 26 |
| 6ix | m-Cl | 32 |

TABLE 3-continued

Yields observed in the last step of the parallel synthesis.

| Compound | R$_1$ | Yield (%) |
|---|---|---|
| 6x | o-F | 10 |
| 6xi | m-F | 10 |

5-(2"-Hydroxy-naphthalen-1-ylmethyl)-2-thioxo-6-o-tolyl-2,3-dihydro-1H-pyrimidin-4-one (6i)

Yielded 115 mg (0.30 mmol, 57%) as a white powder. m. p. 170-172° C. IR (NaCl, thin layer) v$_{max}$/cm$^{-1}$ 2988 (OH), 2902 (CH$_3$, CH$_2$), 1627 (C=O), 1554 (NH), 1453 (CSNH), 1394 and 1255 (OH), 1211 (C=S), 1075 and 1057 (C—O), 819, 808 and 744 (C—H$_{Ar}$), 729 (C—H). $^1$H NMR (DMSO-$d_6$, 300 MHz): δ=12.60 (br, 1H, NH), 12.17 (br, 1H, NH), 9.21 (br, 1H, OH), 7.63 (d, 1H, J=8.1 Hz, H-5"), 7.43 (d, 1H, J=8.8 Hz, H-4"), 7.39 (d, 1H, J=7.4 Hz, H-8"), 7.26-7.08 (m, 3H, H-6", H-7"+ArH), 7.03-6.99 (m, 2H, ArH), 6.90 (d, 1H, J=7.1 Hz, ArH), 6.78 (d, 1H, J=8.8 Hz, H-3"), 3.88 (q, 1H, H-1"), 1.62 (s, 3H, CH$_3$). $^{13}$C NMR (100 MHz, DMSO-$d_6$): δ=173.3 (C=S), 162.4 (C=O), 152.6 (C2"), 150.0 (C6), 135.6 (C2'), 132.9 (C1'), 131.0 (C8"a), 129.2 (Ar), 129.0 (Ar), 128.4 (C5"), 128.0 (C4"), 127.8 (C4"a), 127.2 (Ar), 125.4 (C7"), 125.1 (Ar), 122.6 (C8"), 121.8 (C6"), 117.8 (C3"), 116.0 (C5), 115.9 (C1"a), 20.1 (C1"), 18.36 (CH$_3$). LR MS [ES$^+$]: m/z 397.12 [M+Na]$^+$ (100%).

5-(2"-Hydroxy-naphthalen-1-ylmethyl)-2-thioxo-6-m-tolyl-2,3-dihydro-1H-pyrimidin-4-one (6ii)

Yielded 54 mg (0.14 mmol, 51%) as a white powder. m. p. 235-237° C. IR (NaCl, thin layer) v$_{max}$/cm$^{-1}$ 3767 and 2988 (OH), 2902 (CH$_3$, CH$_2$), 1646 (C=O), 1563 (NH), 1465 (CSNH), 1403, 1394 and 1233 (OH), 1211, 1198 and 1128 (C=S), 1066, 1044 and 1017 (C—O), 993 (C—H), 823 and 747 (C—H$_{Ar}$). $^1$H NMR (DMSO-$d_6$, 300 MHz): δ=12.55 (br, 1H, NH), 12.22 (br, 1H, NH), 9.41 (br, 1H, OH), 7.65 (d, 1H, J=7.9 Hz, H-5"), 7.47 (d, 1H, J=8.8 Hz, H-4"), 7.36 (d, 1H, J=8.5 Hz, H-8"), 7.26-7.09 (m, 4H, H-7", H-6"+2×ArH), 7.00-6.96 (m, 1H, ArH), 6.93-6.85 (m, 2H, H-3"+1×ArH), 3.91 (s, 2H, H-1"), 2.18 (s, 3H, CH$_3$). $^{13}$C NMR (100 MHz, DMSO-$d_6$): δ=173.8 (C=S), 162.4 (C=O), 152.7 (C2"), 150.9 (C6), 136.9 (C3'), 133.0 (C8"a), 131.5 (C1'), 129.9 (C2'), 128.9 (Ar), 128.3 (C4a), 128.0 (C4"), 127.6 (C5"), 127.4 (Ar), 126.2 (Ar), 125.4 (C7"), 122.7 (C8"), 121.8 (C6"), 118.2 (C3"), 116.5 (C1"), 115.0 (C5), 21.3 (C1"a), 20.2 (CH$_3$). LR MS [ES$^+$]: m/z 397.10 [M+Na]$^+$ (100%).

5-(2"-Hydroxy-naphthalen-1-ylmethyl)-2-thioxo-6-p-tolyl-2,3-dihydro-1H-pyrimidin-4-one (6iii)

Yielded 56 mg (0.15 mmol, 50%) as a white powder. m. p. >250° C. (decomposes). m. p. 220-221° C. IR (NaCl, thin layer) v$_{max}$/cm$^{-1}$ 3663 and 2988 (OH), 2902 (CH$_3$, CH$_2$), 1630 (C=O), 1540 (NH), 1515 (CSNH), 1445 (C—N), 1405, 1349 and 1250 (OH), 1226 and 1208 (C=S), 1066 and 1028 (C—O), 818, 744 and 729 (C—H$_{Ar}$). $^1$H NMR (DMSO-$d_6$, 300 MHz): δ=12.52 (br, 1H, NH), 12.26 (br, 1H, NH), 9.46 (br, 1H, OH), 7.65 (d, 1H, J=7.4 Hz, H-5"), 7.50 (d, 1H, J=8.7 Hz, H-4"), 7.35 (d, 1H, $^3$J=7.7 Hz, H-8"), 7.22-7.08 (m, 6H, H-7", H-6"+4×ArH), 6.92 (d, 1H, J=8.7 Hz, H-3"), 3.89 (s, 2H, H-1"), 2.29 (s, 3H, CH$_3$). $^{13}$C NMR (100 MHz, DMSO-$d_6$): δ=173.8 (C=S), 162.2 (C=O), 152.7 (C2"), 150.1 (C6), 139.1 (C4'), 133.0 (C8"a), 128.7 (C4"a), 128.5 (Ar), 128.4 (Ar), 128.0 (C5"), 127.4 (C4"), 125.7 (C7"), 122.8 (C8"), 121.8 (C6"), 118.4 (C3") 116.5 (C1"), 115.1 (C5), 21.1 (CH$_2$), 20.9 (CH$_3$). Carbon C' was not observed in this spectrum. LR MS [ES$^+$]: m/z 397.09 [M+Na]$^+$ (100%).

6-(4'-Chloro-phenyl)-5-(2"-hydroxy-naphthalen-1-ylmethyl)-2-thioxo-2,3-dihydro-1H-pyrimidin-4-one (61v)

Yielded 20 mg (0.05 mmol, 18%) as a white powder after column chromatography (EtOAc-hexane 1:2). m. p. >287-289° C. IR (NaCl, thin layer) v$_{max}$/cm$^{-1}$ 3277 and 3030 (OH), 2941 (CH$_2$), 1702 and 1633 (C=O), 1545 (NH), 1448 (C—N), 1219 and 1204 (C=S, CSNH), 1114, 1127 and 1090 (C=S), 1090 and 1014 (C—O), 837 and 820 (C—H$_{Ar}$). $^1$H NMR (400 MHz, DMSO-$d_6$): δ=12.57 (br, 1H, NH), 12.23 (br, 1H, NH), 9.38 (s, 1H, OH), 7.64 (d, 1H, J=7.5 Hz, H-5"), 7.49-7.41 (m, 2H, H-4", H-8"), 7.30-7.22 (m, 1H, H-7"), 7.21-7.14 (m, 3H, H-6" overlapping with AA'BB' system, J=8.3 Hz, H-3", H-5"), 7.04 (d, 2H, J=8.3 Hz, AA'BB' system, H-2', H-6'), 6.85 (d, 1H, J=8.7 Hz, H-3"), 3.91 (s, 2H, H-1"). LR MS [ES$^-$]: m/z 393.13 [M−H]$^-$ (100%).

5-((2"-hydroxynaphthalen-1-yl)methyl)-6-(4'-iodophenyl)-2-thioxo-2,3-dihydropyrimidin-4(1H)-one (6v)

Yielded 13 mg (0.02 mmol, 22%) as a white powder after precipitation. Purified by column chromatography (EtOAc-Hexane, 1:2). IR (NaCl, thin layer) v$_{max}$/cm$^{-1}$ 3090 (OH), 1628 (C=O), 1560 (NH), 1427 (C—N), 1208 (C=S, CSNH), 1154 and 1126 (C—O, C=S), 1008 (C—O), 850, 814 and 754 (C—H$_{Ar}$). $^1$H NMR (400 MHz, Acetone-$d_6$): δ=11.62 (br, 1H, NH), 12.27 (br, 1H, NH), 9.33 (s, 1H, OH), 7.70-7.55 (m, 3H, H-4", H-5", H-8"), 7.35-6.98 (m, 7H, H-8", H-7", H-3"+4×ArH), 4.08 (s, 2H, H-1"). LR MS [ES$^+$]: m/z 508.02 [M+Na]$^+$ (100%).

5-(2"-Hydroxy-naphthalen-1-ylmethyl)-2-thioxo-6-(4'-trifluoromethyl-phenyl)-2,3-dihydro-1H-pyrimidin-4-one (6vi)

Yielded 33 mg (0.077 mmol, 25%) as a white powder after column chromatography (EtOAc-hexane, 1:2). m. p. >250° C. IR (NaCl, thin layer) v$_{max}$/cm$^{-1}$ 2970 (OH), 2912 (CH$_2$), 1691, 1549 and 1428 (C—N), 1635 (C=O), 1515 (CSNH), 1409 (OH), 1321, 1286 and 1167 (C—F), 1131 and 1112 (C=S), 1065 and 1017 (C—O), 860 and 702 (C—H), 821, 778 and 743 (C—H$_{Ar}$). $^1$H NMR (400 MHz, DMSO-$d_6$): δ=12.67 (br, 1H, NH), 12.28 (br, 1H, NH), 9.40 (br, 1H, OH), 7.65 (d, 1H, J=8.3, H-5"), 7.52-7.35 (m, 4H, H-4" and H-8" overlapped with AA'BB' system, J=8.0 Hz, H-2', H-6'), 7.17 (m, 1H, m $^3$J=6.9 Hz, H-7"), 7.17-7.12 (m, 3H, H-6" overlapped with 2×Ar, AA'BB' system, J=8.0 Hz, H-3', H-5'), 6.80 (d, 1H, J=8.8 Hz, H-3"), 3.95 (s, 2H, H-1"). $^{13}$CNMR (100 MHz, DMSO-$d_6$): δ=173.9 (C=S), 161.9 (C=O), 152.2 (C2"), 148.8 (C6), 135.3 (C1'), 132.9 (C8"a), 129.3 (C4'), 128.8 (C3', C5'), 128.0 (C4"), 127.9 (C5"), 127.8 (C4"a), 125.6 (C7"), 124.1 (C2", C6"), 122.6 (C6"), 121.9 (C8"), 119.8 (CF$_3$), 117.6 (C3"), 116.2 (C1"a), 116.0 (C5), 20.54 (C1"). LR MS [ES$^+$]: m/z 451.05 [M+Na]$^+$ (100%).

6-(2'-Bromo-phenyl)-5-(2"-hydroxy-naphthalen-1-ylmethyl)-2-thioxo-2,3-dihydro-1H-pyrimidin-4-one (6vii)

Yielded 30 mg (0.07 mmol, 20%) after purification by column chromatography and recrystallisation from CHCl$_3$.

m. p. 224-226° C. IR (NaCl, thin layer) $v_{max}$/cm$^{-1}$ 3055 (OH), 2927 (CH$_2$), 1627 (C=O), 1548 (N—H), 1436 (C—N), 1196 (C=S, CSNH), 1132 and 1117 (C—O, C=S), 1027 (C—O), 813 and 740 (C—H$_{Ar}$), 678 (C—Br). $^1$H NMR (Acetone-$d_6$, 300 MHz): δ=11.61 (br, 1H, NH), 11.23 (br, 1H, NH), 8.93 (br, 1H, OH), 7.74-7.60 (m, 1H, H-5'), 7.61-7.52 (m, 2H, H-4", H-8"), 7.38-7.11 (m, 6H, H-6", H-7"+ArH×4), 6.88 (d, 1H, J=8.8 Hz, H-3"), 4.13 (d, 1H, AB system, J=15.6 Hz, H-1"), 3.98 (d, 1H, AB system, J=15.6 Hz, H-1"). $^{13}$C NMR (DMSO-$d_6$, 100 MHz): 175.3 (C=S), 164.5 (C=O), 154.6 (C2"), 150.6 (C6), 134.4 (C1'), 133.4 (C8"a), 133.6 (Ar), 131.9 (Ar), 132.5, (Ar), 129.9 (C4"a), 129.1 (C4"), 129.0 (Ar), 128.3 (C5"), 126.7 (C7"), 123.6 (C8), 123.3 C2"), 123.1 (C6"), 119.7 (C3"), 117.0 (C1"a), 117.0 (C5), 21.4 (C1"). LR MS [ES$^+$]: m/z 460.92, 462.92 [M+Na]$^+$ (100%); LR MS [ES$^-$]: m/z 437.01, 439.01 [M−H]$^-$ (100%); HR MS [ES$^+$]: m/z calc'd for C$_{21}$H$_{15}$N$_2$O$_2$SNa$^{79}$Br 460.9935[M+Na]$^+$. found 460.9941 (+1.3 ppm); m/z calc'd for C$_{21}$H$_{15}$N$_2$O$_2$SNa$^{81}$Br 462.9915 [M+Na]$^+$. found 462.9903 (−2.6 ppm).

6-(3'-Bromo-phenyl)-5-(2"-hydroxy-naphthalen-1-ylmethyl)-2-thioxo-2,3-dihydro-1H-pyrimidin-4-one (6viii)

Yielded 15 mg (0.07 mmol, 26%) as a white powder after column chromatography (EtOAc-hexane 1:2) and recrystallised from CHCl$_3$. m. p. >237-239° C. IR (NaCl, thin layer) $v_{max}$/cm$^{-1}$ 3114 and 3081 (OH), 2935 (CH$_2$), 1713 and 1629 (C=O), 1561 (NH), 1462 and 1439 (C—N), 1199 (C=S, CSNH), 1119 (C—O, C=S), 820, 806 and 746 (C—H$_{Ar}$), 697 (C—Br). $^1$H NMR (400 MHz, DMSO-d$_6$): δ=12.58 (br, 1H, NH), 12.21 (br, 1H, NH), 9.36 (s, 1H, OH), 7.63 (d, 1H, J=7.7 Hz, H-5"), 7.51-7.47 (m, 2H, H-4", H-8"), 7.40-7.35 (m, 1H, ArH), 7.31-7.25 (m, 1H, H-7"), 7.20-7.15 (m, 1H, H-6"), 7.12-6.99 (m, 3H, ArH), 6.85 (d, 1H, J=8.8 Hz, H-3"), 3.91 (s, 2H, H-1"). $^{13}$C NMR (100 MHz, Acetone-d$_6$): δ=175.3 (C=S), 164.7 (C=O), 154.3 (C2"), 150.5 (C6), 134.8 (C1'), 134.3 (C8"a), 134.0 (CAr), 132.7 (CAr), 131.2 (CAr), 130.0 (C4"a), 129.3 (CAr), 129.2 (C4"), 128.8 (C5"), 126.6 (C7"), 123.8 (C8"), 123.3 (C6"), 122.7 (C3"), 120.3 (C3"), 117.9 (C1"a), 116.0 (C5), 22.2 (C1"). LR MS [ES$^-$]: m/z 436.99 [M−H]$^-$, 439.00 [M−H]$^-$; HR MS [ES$^-$]: m/z calc'd for C$_{21}$H$_{14}$N$_2$O$_2$S$^{79}$Br 436.9959 [M−H]$^-$. found 436.9966 (+1.5 ppm); m/z calc'd for C$_{21}$H$_{14}$N$_2$O$_2$S$^{81}$Br 438.9939 [M−H]$^-$. found 438.9948 (+2.1 ppm).

6-(3'-Chloro-phenyl)-5-(2"-hydroxy-naphthalen-1-ylmethyl)-2-thioxo-2,3-dihydro-1H-pyrimidin-4-one (6ix)

Yielded 18 mg (0.004 mmol, 32%) as a white powder after column chromatography (EtOAc-hexane, 1:2) and recrystallisation from CHCl$_3$. m. p. >229-232° C. IR (NaCl, thin layer) $v_{max}$/cm$^{-1}$ 3086 (OH), 2941 (CH$_2$), 2363, 1635 (C=O), 1556 (NH) 1439 (C—N), 1257 and 1213 (C=S, CSNH), 1129 (C—O), 1041 and 1027 (C—O), 819, 750 (C—H$_{Ar}$). $^1$H NMR (Acetone-$d_6$, 400 MHz): δ=11.59 (br, 1H, NH), 11.22 (br, 1H, NH), 9.25 (s, 1H, OH), 7.68 (d, 1H, J=7.6 Hz, H-5"), 7.57 (d, 1H, J=8.8 Hz, H-4"), 7.53-7.40 (m, 4H, H-8"3×ArH), 7.23-7.08 (m, 3H, H-7", H-6"+1×ArH), 7.00 (d, 1H, J=8.8 Hz, H-3"), 3.92 (s, 2H, H-1"). $^{13}$C NMR (Acetone-$d_6$, 100 MHz): δ=175.0 (C=S), 164.7 (C=O), 154.3 (C2"), 150.6 (C6), 134.7 (C3'), 134.5 (C1'), 133.5 (C8"a), 131.1 (Ar), 131.0 (Ar), 131.0 (Ar), 130.0 (C4"a), 129.9 (Ar), 129.3 (C4"), 129.2 (C5"), 128.3 (Ar), 126.6 (C7"), 123.8 (C8"), 123.3 (C6"), 120.1 (C3"), 117.8 (C1"a), 116.0 (C5), 22.1 (C1"). LR MS [ES$^-$]: m/z 393.12 [M−H]$^-$ (100%); LRMS [ES$^+$]: 417.10 [M+Na]$^+$ (100%). HR MS [ES$^-$]: m/z calc'd for C$_{21}$H$_{14}$N$_2$O$_2$SCl 393.0465 [M−H]$^-$. found 393.0461 (−0.9 ppm).

6-(2'-Fluoro-phenyl)-5-(2"-hydroxy-naphthalen-1-ylmethyl)-2-thioxo-2,3-dihydro-1H-pyrimidin-4-one (6x)

Yielded 17 mg (0.10 mmol, 10%) as a white powder after column chromatography (EtOAc-Hexane 1:2) and recrystallisation from CHCl$_3$. m p 197° C. (decomposes). IR (NaCl, thin layer) $v_{max}$/cm$^{-1}$ 3316 and 2935 (OH), 2885 (CH$_2$), 1630 (C=O), 1558 (NH), 1439 (C—N), 1269 and 1216 (C—F), 1131 (C—O, C=S) 816 and 751 (C—H$_{Ar}$). $^1$H NMR (400 MHz, DMSO-d$_6$): δ=12.61 (br, 1H, NH), 12.35 (br, 1H, NH), 9.27 (s, 1H, OH), 7.63 (d, 1H, J=7.3 Hz, H-5"), 7.53-7.43 (m, 2H, H-4"+ArH), 7.30-7.22 (m, 2H, H-7"+1×ArH), 7.17-7.12 (m, 1H, H-6"), 7.13-7.05 (m, 1H, H-7"), 7.00-6.92 (m, 2H, ArH), 6.82 (d, 1H, J=8.8 Hz, H-3"), 3.90 (s, 2H, CH$_2$). $^{13}$C NMR (100 MHz, DMSO-d$_6$): δ=173.3 (C=S), 161.9 (C=O), 159.9 (C2'), 157.4 (C6), 152.7 (C2"), 132.9 (C8"a), 131.5 (C6'), 130.3 (C4'), 128.0 (C5"), 127.8 (C4"a), 127.4 (C4"), 125.4 (C7"), 123.7 (C5'), 122.6 (C8"), 121.8 (C6"), 121.7 (C1'), 117.7 (C3"), 117.2 (C5), 115.8 (C3'), 115.1 (C1"a), 20.5 (C1"). LR MS [ES$^-$]: m/z 377.14 [M−H]$^-$ (100%); LR MS [ES$^+$]: m/z 401.10 [M+Na]$^+$ (100%). HR MS [Cl$^+$]: m/z calc'd for C$_{21}$H$_{16}$N$_2$O$_2$SF 379.0917 [M+H]$^+$. found 379.0911 (−1.5 ppm).

6-(3'-Fluoro-phenyl)-5-(2"-hydroxy-naphthalen-1-ylmethyl)-2-thioxo-2,3-dihydro-1H-pyrimidin-4-one (6xi)

Yielded 18 mg (0.10 mmol, 10%) as white powder after column chromatography (EtOAc-hexane 1:2) and recrystallisation from CHCl$_3$. m. p. 150° C. (decomposes). IR (NaCl, thin layer) $v_{max}$/cm$^{-1}$ 3378, 3126, 3059 (OH), 2941 (CH$_2$), 1630 (C=O), 1554 (NH), 1439 (C—N), 1268 (C—F), 1199 (C=S, CSNH), 1158 and 1119 (C—O, C=S), 821, 792 and 746 (C—H$_{Ar}$). $^1$H NMR (400 MHz, DMSO-d$_6$): δ=12.58 (br, 1H, NH), 12.24 (br, 1H, NH), 9.41 (s, 1H, OH), 7.64 (d, 1H, J=7.5 Hz, H-5"), 7.48-7.45 (m, 2H, H-4", H-8"), 7.30-6.99 (m, 4H, H-7", H-6"+2×ArH), 6.93-6.68 (m, 3H, H-3"+2×ArH), 3.92 (s, 2H, H-1). $^{13}$C NMR (100 MHz, DMSO-d$_6$): δ=173.8 (C=S), 162.6 (C3'), 162.1 (C=O), 159.5 (C6), 152.7 (C2"), 134.1 (C1'), 133.0 (C8"a), 129.7 (CAr), 128.1 (C5"), 128.0 (C4a), 127.5 (C4"), 125.6 (C7"), 124.4 (C6'), 122.8 (C8"), 121.9 (C6"), 117.9 (C3"), 116.3 (C1"a), 116.0 (CAr), 115.7 (C5), 115.4 (CAr), 20.8 (C1"). HR MS [ES$^+$]: m/z calc'd for C$_{21}$H$_{15}$N$_2$O$_2$NaSF 401.0736 [M+Na]$^+$. found 401.0735 (−0.2 ppm).

In Vitro Inhibition of SIRT1 and SIRT2 by Cambinol Analogs 6i-Xi and 6a-6j

TABLE 4

Biological properties of compounds 6i-xi and 6a-6j
Inhibition at 60 μM ± SE$^a$ (%)

| Compound[e] | R' | R$^1$ | Y | SIRT1[d] | IC$_{50}$[b] | SIRT2[d] | IC$_{50}$[b] |
|---|---|---|---|---|---|---|---|
| 1[c] | H | H | S | 59.5 ± 1 | 40.7 ± 11 | 51.9 ± 1 | 47.9 ± 12 |
| 6a[c] | H | H | O | 15.5 ± 2 | — | 6.5 ± 4 | — |
| 6b | p-Br | H | S | 82.3 ± 1 | 12.7 ± 2 | 9.4 ± 1 | >90 |
| 6c[c] | p-CH$_3$O | H | S | 6.4 ± 1 | — | 9.2 ± 2 | — |

TABLE 4-continued

Biological properties of compounds 6i-xi and 6a-6j
Inhibition at 60 μM ± SE$^a$ (%)

| Compound$^e$ | R' | R$^1$ | Y | SIRT1$^d$ | IC$_{50}$$^b$ | SIRT2$^d$ | IC$_{50}$$^b$ |
|---|---|---|---|---|---|---|---|
| 6d$^c$ | H | H | S | 37.8 ± 1 | — | 52.7 ± 2 | — |
| 6i | o-CH$_3$ | H | S | 79.6 ± 1 | 43.0 ± 2 | 29.1 ± 2 | — |
| 6ii | m-CH$_3$ | H | S | 83.2 ± 4 | 44.2 ± 2 | 12.7 ± 2 | — |
| 6iii | p-CH$_3$ | H | S | 79.0 ± 2 | 44.5 ± 1 | 13.4 ± 3 | — |
| 6iv$^c$ | p-Cl | H | S | 13.7 ± 1 | — | 20.1 ± 1 | — |
| 6v$^c$ | p-I | H | S | 7.7 ± 1 | — | 7.7 ± 1 | — |
| 6vi$^c$ | p-CF$_3$ | H | S | 15.1 ± 1 | — | 6.7 ± 1 | — |
| 6vii$^c$ | o-Br | H | S | 19.7 ± 1 | — | — | — |
| 6viii$^c$ | m-Br | H | S | 4.8 ± 1 | — | 6.6 ± 3 | — |
| 6ix$^c$ | m-Cl | H | S | 11.3 ± 1 | — | 7.6 ± 6 | — |
| 6x | o-F | H | S | 89.0 ± 1 | 50.0 ± 1 | 19.5 ± 1 | — |
| 6xi | m-F | H | S | 87.8 ± 1 | 38.3 ± 1 | 52.1 ± 1 | — |
| 6e | H | Me | S | 29.4 ± 1 | >90 | 80.4 ± 1 | 20.1 ± 5 |
| 6f | H | Et | S | 31.9 ± 1 | — | 86.8 ± 1 | 10.5 ± 3 |
| 6g | H | Allyl | S | 37.5 ± 1 | — | 88.3 ± 1 | 22.2 ± 1 |
| 6h | H | n-Prop | S | 25.0 ± 2 | — | 94.7 ± 1 | 4.8 ± 2 |
| 6j | H | n-But | S | 16.9 ± 1 | — | 97.6 ± 1 | 1.0 ± 1 |

$^a$SE, standard error (n = 2).
$^b$IC$_{50}$ were determined for compounds that had over 60% inhibition at 60 μM for SirT1 and SirT2 (repeated at least two times);
(—) not determined.
$^c$Compounds 1 (cambinol), 6a, 6c, 6d, 6iv-ix, not examples of the invention but useful for understanding and practising it.
$^d$Inhibitory activity recorded as percentage of inhibition at 60 μM concentration in duplicate.
$^e$X = O; each R$^2$ = H, each Ar phenyl substituted where indicated or unsubstituted (H) and Ar' = β-naphthol in all compounds except compound 6d in which Ar' = 2-hydroxy, 5-phenyl (phenyl).

Cambinol (1) and its analogs were tested for activity in vitro against SirT1 and SirT2 (Table 4). The IC$_{50}$ values observed in these experiments with 1 were similar to those previously reported (Heltwig et al., infra) (40.7±11 vs 56 μM for SirT1 and 47.9±12 vs 59 μM for SIRT2). In initial studies, introduction of a p-methoxy substituent in the phenyl ring of 1 to give 6c led to a loss of activity against SIRT1 and SIRT2. Interestingly, only activity against SIRT2 was lost when a methyl substituent was incorporated at the para or any other position in the aromatic ring (6i-6iii) with these 3 analogs clearly demonstrating selective inhibition of SIRT1. The p-bromine analog 6b also exhibited relatively selective inhibition of SIRT1 (IC$_{50}$=12.7±2 μM) compared with SirT2 (IC$_{50}$>90 μM). The IC$_{50}$ value attributed to 6b represents a 4-fold improvement in activity against SIRT1 compared with cambinol (1). Replacement of the p-bromine substituent in 6b with chlorine, iodine or trifluoromethyl (6iv, 6v or 6vi respectively) led to a significant decrease in activity for both enzymes. The position of the bromine group in 6b was also important as SIRT1 activity was lost when this substituent was placed at either the o- or m-position of the aromatic ring (analogs 6vii and 6viii). Incorporation of a m-chloro-substituted in analog 6ix also reduced activity against SIRT1 and SIRT2. The use of a fluorine substituent to reduce electron density without an increase in steric bulk led to analogs 6x and 6xi with comparable activity against SIRT1 to 1 implying that the improved activity of the p-bromine analog 6b results from a gain of an additional hydrophobic interaction rather than through a reduction in electron density associated with the aromatic ring. Previous studies have reported that when the β-naphthol ring in cambinol (1) is replaced by a phenol ring activity against SIRT1 and SIRT2 is lost. The observed reduction in activity of the biphenyl-4-ol-containing analog 6d against SIRT1 compared to 1 supports the view that the β-naphthol ring in 1 is a good pharmacophore for activity against this enzyme. Importantly, however, observed retention of activity against SIRT2 suggests this isoform is more tolerant to change at this position in 1. Moreover, however, it is clear that the β-naphthol ring is not essential even against SIRT 1 since activity is not lost completely: rather it is reduced. Substitution of the thiocarbonyl functionality in 1 for a carbonyl group (6a) resulted in significantly reduced activity against both enzymes. The incorporation of a N1-methyl substituent in analog 6e led to an increase in activity against SIRT2 (IC$_{50}$=20.1±5 μM c.f. 47.9±12 μM for 1) and to a decrease in potency against SIRT1 (IC$_{50}$>90 μM for 6e). As a result of these changes in activity compared to cambinol (1), 6e is a selective SIRT2 inhibitor in vitro. This result led to the synthesis of four other analogs 6f,g,h,j with different aliphatic chains at the N1-position each with potency against SIRT2 was observed. The N1-butyl analog 6j is the most potent inhibitor of SirT2 identified to date in this inhibitor class with an IC$_{50}$=0.4 μM±12 for SIRT2 whilst demonstrating poor inhibition of SIRT1 (Table 4). The majority of the synthetic intermediates prepared en route to analogs of 1 were also tested against SirT1 at least in duplicate at 60 μM concentration. No active compounds were identified due to the structural similarity to splitomicin.

Identification of a Potential Binding Mode.

In order to provide a potential rationalisation for the observed in vitro activity and selectivity of cambinol (1) and its analogs, automated ligand docking studies were carried out using the software GOLD. The reported structure of human SIRT2 was used in this study (PDB ID: 1J8F). All the SIRT2 crystal structures so far determined are characterised by a highly-conserved catalytic domain of 270 amino acids that consists of a large classical Rossman-fold domain and a small zinc binding subdomain. The active site is situated at the interface between the two domains and is commonly divided into A, B and C subpockets into which the substrates and cofactor bind. No ligand bound structures of human SIRT2 have been solved but its homolog from yeast and *Archaeoglobus fulgidus* have been extensively characterised with regard to the mode of substrate and cofactor binding. To date, no crystal structure has been reported for SIRT1.

Recently reported docking studies proposed that 1 binds in the nicotinamide C-subpocket of the catalytic domain of SIRT2. Whilst no direct evidence to support this binding mode was provided, our attempts to identify a binding mode for 1 using GOLD led to an analogous result. In our hands, 1 gives lowest energy solutions when bound in the C-pocket, oriented such that the β-napthol ring is sandwiched between the two aromatic residues Phe119 and His187 with π-stacking interactions probably contributing to the calculated stability of this binding mode. It is in this pocket that the acetylated lysine of SIRT2 substrates bind. In addition, we observed that the polar component of cambinol (1), represented by the carbonyl, the thiocarbonyl groups and the two nitrogen atoms, have the potential to form hydrogen bonds to the active site. Although our model did not include water molecules in the active site, the predicted orientation of this part of the ligand is in close agreement with that proposed previously. It is of interest that our small molecule x-ray structure of 1 in the absence of protein identifies the existence of an intramolecular hydrogen bond between the phenolic OH and the carbonyl group. When this conformation of 1 was used as the starting point for the docking studies, rather than the lowest energy conformation predicted by the PRODRG server, analogous results were obtained suggesting that loss of this hydrogen bond can be accommodated for on binding to the protein. In general, visual analysis of the highest scoring docking poses for the new analogs of 1 showed a very similar situation to that previously reported and found by us for cambinol (1) itself, with all the new inhibitors showing the same preferred binding mode with the β-naphthol ring sandwiched in the previously identified hydrophobic channel between Phe119 and His 187. Modest differences in the conformation of the f3-naphthol moiety of the inhibitors were observed.

Rationalisation of the Observed Increase in SIRT2 Selectivity and Activity Associated with an N1-Substituent Without wishing to be bound by theory, the improvement in the inhibitory activity and selectivity observed for analogs 6e and 6f-j against SIRT2 can be rationalised by the formation of additional hydrophobic interactions between the N1 substituent and a previously unoccupied narrow liphophilic channel around Phe 96, Leu138 and Ile 169 in the SIRT2 active site (FIG. 1). The proposed binding mode of this subset of analogs was observed consistently during the docking studies. It is interesting to note that a structure of the *Archaeoglubos fulgidus* enzyme has been solved in which this channel is occupied by a pentaethylene glycol molecule (PDB ID: 1S7G).

Rationalisation of the Observed Variation in Activity for Analogs Incorporating a Substituent in the Phenyl Ring of 1

Without wishing to be bound by theory, a key conclusion from the SAR data (Table 4) was the increase in potency and net SIRT1 selectivity associated with the incorporation of a p-bromine substituent (6b) into the phenyl ring of 1. Visual analysis of the docking poses for N1-substituted analogues suggested that the active site of SIRT2 is too small to accommodate a phenyl ring bearing a large p-substituent consistent with the observed relative lack of activity against SIRT2 of the p-bromine (6b) and p-iodine (6v) analogs. Although the majority of the amino acids in this region are conserved between SIRT2 and SIRT1, again the structural variation of the 96-loop could account for the observed selectivity. Within this loop, Tyr104 points directly into the pocket that is predicted to accommodate the phenyl ring of 1. Due to the predicted structural alteration of the 96-loop between SIRT2 and SIRT1, this pocket has the potential to be larger in SIRT1 compared to SIRT2 with the pocket now being able to accommodate the p-bromine substituent.

Figure 2:
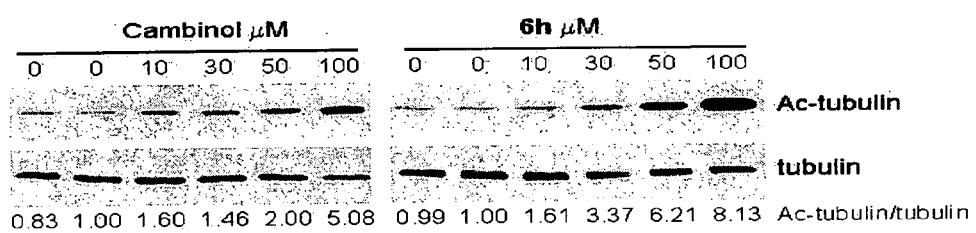
FIG. 2 shows two gels evidencing increased levels of acetylated α-tubulin within HT299 cells treated with a compound of the invention (right hand gel) as compared with cambinol (left hand gel). Total tubulin was used as a loading control.
Figure 3:
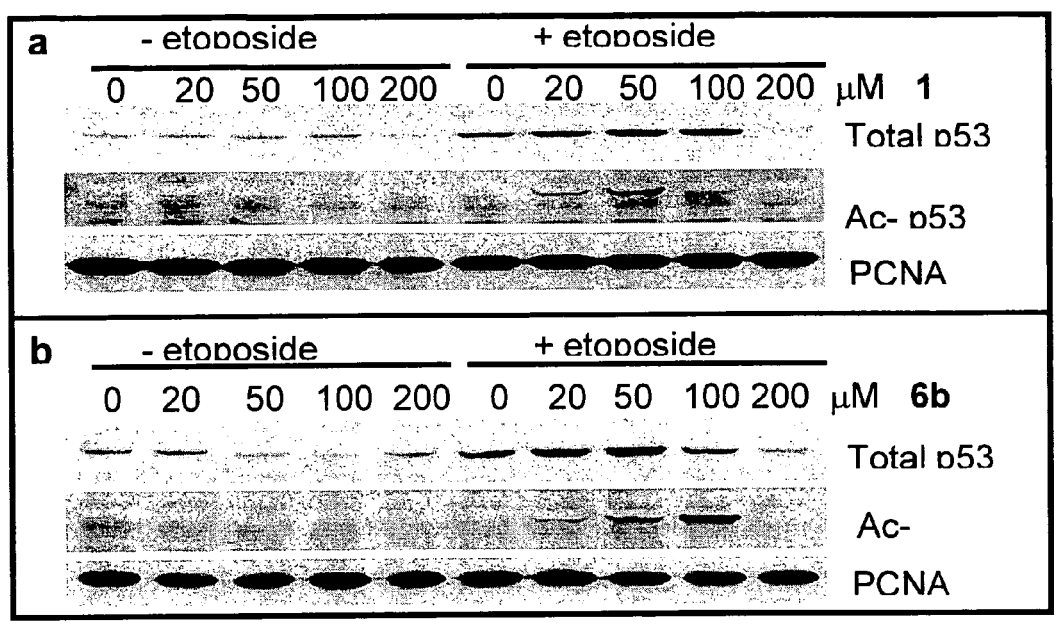
FIG. 3 shows expression of p53 and acetylated p53 in MCF-7 breast adenocarcinoma cells treated with different concentrations of cambinol (a) and a compound of the inventions (b). Additionally, cells were treated with the same compounds in the presence of the genotoxic agent etoposide.

We have thus tuned the essentially unselective cambinol (1) into analogs that demonstrate either SIRT1 (6b) or SIRT2 (6h,j) selective properties in vitro. Further evidence to support the selective targeting of SIRT1 and SIRT2 by these analogs came from studies in cells. In a previous report, Bedalov and co-workers detected higher levels of p53 and acetylated p53 in NCl H460 cancer cells treated with cambinol (1) in the presence of the genotoxic agent etoposide (10 μM) (Heltweg et al., infra). Here we tested our new selective SirT1 inhibitor 6b for this effect in cells and compared it to cambinol (1). As previously observed for cambinol (1), in the presence of the genotoxic agent etoposide (10 μM), the levels of p53 were increased with maximal p53 levels being observed at 50 μM of 1However, in the presence of etoposide, and like cambinol (1), compound 6b also increased p53 levels. When the levels of p53 acetylated at lysine 382 were analysed, 6b showed a clear increase in potency compared to cambinol (1). These data are shown in FIG. 3. As expected for a selective SIRT1 inhibitor, 6b did not lead to an increase in acetylation of tubulin when H1299 cells were treated with 6b and Trichostatin A (an inhibitor of class I and II HDACs). When this experiment was repeated, this time using the SIRT2 selective inhibitor 6h, a significant increase in the levels of acetylated tubulin was achieved compared with the effect of cambinol (1) see FIG. 2. These results shows that the SirT2 selective inhibitor 6h is cell-permeable and provides a good correlation between in vitro selectivity profiles for cambinol, 6b and 6h further strengthening the view that the cambinol class of compounds impair sirtuin activity in vivo.

The invention claimed is:

1. A compound according to formula (I):

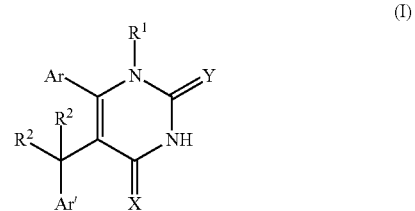

wherein:
X is O or S;
Y is O or S;
each Ar and Ar' is independently a mono-, bi- or tricyclic aryl or heteroaryl group optionally substituted with one or more substituents selected from halo, alkyl, aryl, heteroaryl, hydroxyl, nitro, amino, alkoxy, alkylthio, cyano, thio, ester, acyl and amido, wherein (i) the heteroaryl group comprises one or more nitrogen or oxygen atoms, and the cyclic components of the mono-, bi, or tricyclic aryl and heteroaryl groups comprise 5- and/or 6-membered rings,
each $R^2$ is independently selected from the group consisting of hydrogen, halo, alkyl, aryl, heteroaryl, hydroxyl, nitro, amino, alkoxy, alkylthio, cyano and thio; and
$R^1$ is a straight-chain or branched $C_{1-25}$ alkyl group wherein the alkyl group may be optionally interrupted (i) by replacing one or more of any of the carbon atoms of the alkyl group independently with one of the following diradical moieties: —O—, —S—, —N($R^6$)—, —C(=O)—, —SO$_2$NR$^6$—, —S(O)—, S(O)$_2$—, C(=O)N($R^6$)—, —C(=O)O—, —C(=S)—, —C(=S)O—, —C(=S)S—, —C(=O)S—, —C(=N—OH)—, —C(=N—OR$^6$)—, —C(=NR$^6$)—, —C(=N—NH$_2$)—, —C(=N—NHR$^6$)—, —C(=O)N(R$^6$)C(=O)—, —C(=S)N(R$^6$)C(=S)—, —C(=O)N(R$^6$)C(=S)— and —C(=N—N(R$^6$)$_2$)—, wherein $R^6$ is hydrogen or alkyl, and/or (ii) when $R^1$ possesses at least two carbon atoms, by replacing, of the six carbon atoms of the alkyl group nearest the nitrogen atom to which the alkyl group is attached, either two of these carbon atoms that are adjacent by a 1,2-disubstituted $C_{3-10}$ cycloalkyl, phenyl or monocyclic heteroaryl diradical, or when $R^1$ possesses at least three carbon atoms, three of these carbon atoms that are adjacent by a 1,3-disubstituted $C_{4-10}$ cycloalkyl, phenyl or monocyclic heteroaryl diradical, or when $R^1$ possesses at least four carbon atoms, four of these carbon atoms that are adjacent by a 1,4-disubstituted $C_{5-10}$ cycloalkyl, phenyl or monocyclic six-membered ring heteroaryl diradical, wherein any cyclocoalkyl, phenyl or monocyclic heteroaryl group present may be optionally substituted with one or more substituents selected independently from halo, hydroxyl, nitro, amino, cyano and thio; and wherein one or more of the hydrogen atoms of the alkyl group may be optionally substituted with one or more substituents selected independently from halo, hydroxyl, nitro, amino, cyano and thio,
or a physiologically acceptable salt thereof.

2. The compound of claim 1, or a physiologically acceptable salt thereof, wherein Ar is a monocyclic aryl or heteroaryl group.

3. The compound of claim 2, or a physiologically acceptable salt thereof, wherein Ar is a phenyl group.

4. The compound of claim 1, or a physiologically acceptable salt thereof, wherein Ar is unsubstituted or is substituted once or twice.

5. A compound according to formula (II):

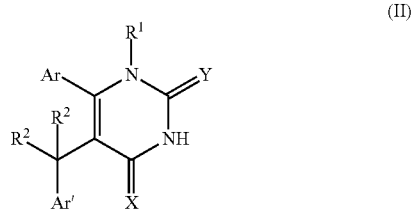

(II)

wherein:
X is O or S;
Y is O or S;
Ar— is selected from the group consisting of:

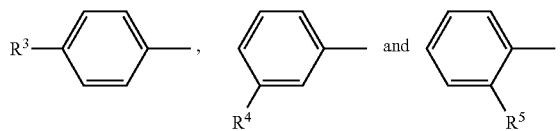

wherein $R^3$ is bromo, fluoro, or alkyl, $R^4$ is fluoro or alkyl and $R^5$ is fluoro or alkyl;

Ar' is independently a mono-, bi- or tricyclic aryl or heteroaryl group optionally substituted with one or more substituents selected from halo, alkyl, aryl, heteroaryl, hydroxyl, nitro, amino, alkoxy, alkylthio, cyano, thio, ester, acyl and amido, wherein (i) the heteroaryl group comprises one or more nitrogen or oxygen atoms, and the cyclic components of the mono-, bi, or tricyclic aryl and heteroaryl groups comprise 5- and/or 6-membered rings;

each $R^2$ is independently hydrogen, halo, alkyl, aryl, heteroaryl, hydroxyl, nitro, amino, alkoxy, alkylthio, cyano and thio; and $R^1$ is hydrogen or a straight-chain or branched $C_{1-25}$ alkyl group wherein the alkyl group may be optionally interrupted (i) by replacing one or more of any of the carbon atoms of the alkyl group independently with one of the following diradical moieties: —O—, —S—, —N($R^6$)—, —C(=O)—, —SO$_2$NR$^6$—, —S(O)—, S(O)$_2$—, C(=O)N($R^6$)—, —C(=O)O—, —C(=S)—, —C(=S)O—, —C(=S)S—, —C(=O)S—, —C(=N—OH)—, —C(=N—OR$^6$)—, —C(=NR$^6$)—, —C(=N—NH$_2$)—, —C(=N—NHR$^6$)—, —C(=O)N(R$^6$)C(=O)—, —C(=S)N(R$^6$)C(=S)—, —C(=O)N(R$^6$)C(=S)— and —C(=N—N(R$^6$)$_2$)—, wherein $R^6$ is hydrogen or alkyl, and/or (ii) when $R^1$ is a straight-chain or branched $C_{1-25}$ alkyl group, and when $R^1$ has at least two carbon atoms, by replacing, of the six carbon atoms of the alkyl group nearest the nitrogen atom to which the alkyl group is attached, either two of these carbon atoms that are adjacent by a 1,2-disubstituted $C_{3-10}$ cycloalkyl, phenyl or monocyclic heteroaryl diradical, or when $R^1$ has at least three carbon atoms, three of these carbon atoms that are adjacent by a 1,3-disubstituted $C_{4-10}$ cycloalkyl, phenyl or monocyclic heteroaryl diradical, or when $R^1$ has at least four carbon atoms, four of these carbon atoms that are adjacent by a 1,4-disubstituted $C_{5-10}$ cycloalkyl, phenyl or monocyclic six-membered ring heteroaryl diradical, wherein any cyclocoalkyl, phenyl or monocyclic heteroaryl group present may be optionally substituted with one or more substituents selected independently from halo, hydroxyl, nitro, amino, cyano and thio; and wherein one or more of the hydrogen atoms of the alkyl group may be optionally substituted with one or more substituents selected independently from halo, hydroxyl, nitro, amino, cyano and thio, or a physiologically acceptable salt thereof.

6. The compound of claim 5, or a physiologically acceptable salt thereof, wherein $R^4$ is fluoro or $C_{1-6}$ alkyl and $R^5$ is fluoro or $C_{1-6}$ alkyl.

7. The compound of claim 6, or a physiologically acceptable salt thereof, wherein $R^4$ is fluoro or methyl and $R^5$ is fluoro or methyl.

8. The compound of claim 5, or a physiologically acceptable salt thereof, wherein $R^3$ is bromo or alkyl.

9. The compound of claim 5, or a physiologically acceptable salt thereof, wherein Ar is para-bromophenyl.

10. The compound of claim 1 or claim 5, or a physiologically acceptable salt thereof, wherein $R^1$ is a straight-chain or branched $C_{1-15}$ alkyl group.

11. The compound of claim 10, or a physiologically acceptable salt thereof, wherein $R^1$ is a straight-chain or branched $C_{1-10}$ alkyl group.

12. The compound of claim 1 or claim 5, or a physiologically acceptable salt thereof, wherein $R^1$ is a straight-chain $C_{1-25}$ alkyl group.

13. The compound of claim 1 or claim 5, or a physiologically acceptable salt thereof, wherein the alkyl group $R^1$ is interrupted by replacing one or more of any of the carbon atoms of the alkyl group independently with one of the following diradical moieties: —O—, —S—, —N($R^6$)—, —C(=O)—, —SO$_2$NR$^6$—, —S(O)—, S(O)$_2$—, C(=O)N($R^6$)—, —C(=O)O—, —C(=S)—, —C(=S)O—, —C(=S)S— and —C(=O)S—.

14. The compound of claim 13, or a physiologically acceptable salt thereof, wherein the alkyl group is interrupted by replacing one or more of any of the carbon atoms of the alkyl group $R^1$ independently with one of the following diradical moieties: —O—, —S—, and —N($R^6$)—.

15. The compound of claim 1 or claim 5, or a physiologically acceptable salt thereof, wherein, when the alkyl group $R^1$ has at least two carbon atoms, of the four carbon atoms of the alkyl group $R^1$ nearest the nitrogen atom to which $R^1$ is attached, either two of these carbon atoms that are adjacent are replaced by a 1,2-disubstituted $C_{3-10}$ cycloalkyl, phenyl or monocyclic heteroaryl diradical, or when the alkyl group $R^1$ has at least three carbon atoms, three of these carbon atoms that are adjacent are replaced by a 1,3-disubstituted $C_{4-10}$ cycloalkyl, phenyl or monocyclic heteroaryl diradical, or when the alkyl group $R^1$ has at least four carbon atoms, four of these carbon atoms that are adjacent are replaced by a 1,4-disubstituted $C_{5-10}$ cycloalkyl, phenyl or monocyclic six-membered ring heteroaryl diradical, wherein any cycloalkyl, phenyl or monocyclic heteroaryl group present may be optionally substituted with one or more substituents selected independently from halo, hydroxyl, nitro, amino, cyano and thio.

16. The compound of claim 1 or claim 5, or a physiologically acceptable salt thereof, wherein none of the six carbon atoms nearest the nitrogen atom to which $R^1$ is attached is replaced by a cycloalkyl, phenyl or monocyclic heteroaryl group.

17. The compound of claim 1 or claim 5, or a physiologically acceptable salt thereof, wherein the alkyl group $R^1$ is not interrupted.

18. The compound of claim 1 or claim 5, or a physiologically acceptable salt thereof, wherein none of the hydrogen atoms of the alkyl group $R^1$ is substituted.

19. The compound of claim 5, or a physiologically acceptable salt thereof, wherein $R^1$ is hydrogen.

20. The compound of claim 1 or claim 5, or a physiologically acceptable salt thereof, wherein X is O.

21. The compound of claim 1 or claim 5 or a physiologically acceptable salt thereof, wherein Y is S.

22. The compound of claim 1 or claim 5, or a physiologically acceptable salt thereof, wherein each $R^2$ is independently selected from the group consisting of H, halo, alkyl, aryl and heteroaryl.

23. The compound of claim 22, or a physiologically acceptable salt thereof, wherein each $R^2$ is independently H or alkyl.

24. The compound of claim 22, or a physiologically acceptable salt thereof, wherein each $R^2$ is H.

25. The compound of claim 1 or claim 5, or a physiologically acceptable salt thereof, wherein Ar' is a bicyclic or tricyclic aryl or heteroaryl group.

26. The compound of claim 25, or a physiologically acceptable salt thereof, wherein Ar' is a bicyclic aryl or heteroaryl group.

27. The compound of claim 26, or a physiologically acceptable salt thereof, wherein Ar' is a bicyclic aryl group.

28. The compound of claim 1 or claim 5, or a physiologically acceptable salt thereof, wherein Ar' is unsubstituted, or is substituted with between one and three substituents.

29. The compound of claim 1 or claim 5, or a physiologically acceptable salt thereof, wherein Ar' is substituted with an amino, hydroxyl or thiol group.

30. The compound of claim 1 or claim 5, or a physiologically acceptable salt thereof, wherein Ar' is substituted only with an amino, hydroxyl or thiol group.

31. The compound of claim 29, or a physiologically acceptable salt thereof, wherein Ar' is substituted with the amino, hydroxyl or thiol group at an atom adjacent to the atom of Ar' connected to remainder of the compound.

32. The compound of claim 29, or a physiologically acceptable salt thereof, wherein Ar' is substituted only with a hydroxyl group.

33. The compound of claim 1 or claim 5, or a physiologically acceptable salt thereof, wherein Ar'— is:

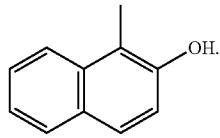

34. A pharmaceutical composition comprising a compound as defined in claim 1 or claim 5, or a physiologically acceptable salt thereof, together with a pharmaceutically acceptable carrier.

35. A method of inhibiting sirtuin activity in a subject, said method comprising administering to a subject a sirtuin-1 (SIRT1) or sirtuin-2 (SIRT2) inhibiting amount of a compound as defined in claim 1 or claim 5, or a physiologically acceptable salt thereof, wherein the compound is effective to inhibit SIRT1 or SIRT2 activity by greater than 60% when evaluated in an in-vitro model at a concentration of 60 μM.

36. The method of claim 35, wherein the compound is effective to inhibit SIRT2 activity and is selected from the group consisting of compounds

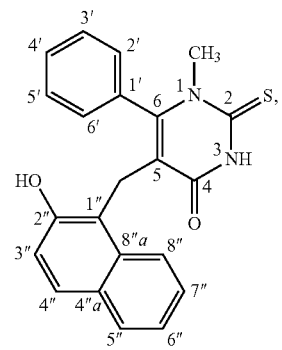

6e

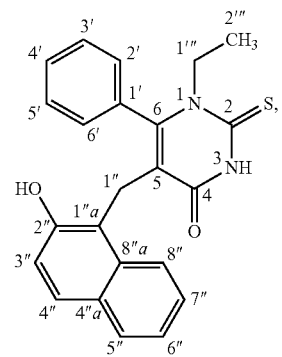

6f

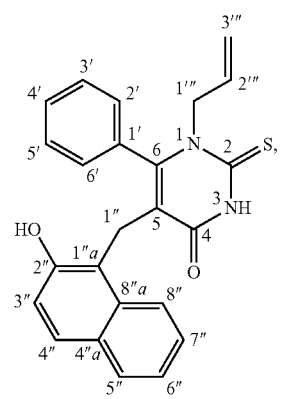

6g

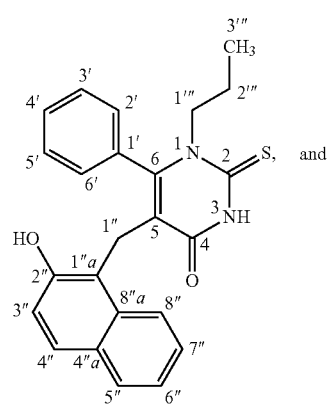

6h and

6j
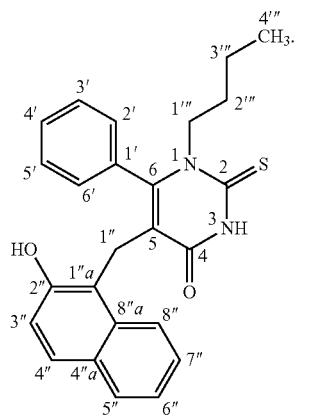
* * * * *

UNITED STATES PATENT AND TRADEMARK OFFICE
CERTIFICATE OF CORRECTION

| | | |
|---|---|---|
| PATENT NO. | : 8,563,557 B2 | Page 1 of 1 |
| APPLICATION NO. | : 13/122097 | |
| DATED | : October 22, 2013 | |
| INVENTOR(S) | : Westwood et al. | |

It is certified that error appears in the above-identified patent and that said Letters Patent is hereby corrected as shown below:

Title page under item (86) PCT No.: change "PCT/GB2009/000236" to --PCT/GB2009/002367--

Signed and Sealed this
Eighteenth Day of February, 2014

Michelle K. Lee
*Deputy Director of the United States Patent and Trademark Office*